US009649353B2

(12) United States Patent
Cunningham

(10) Patent No.: US 9,649,353 B2
(45) Date of Patent: May 16, 2017

(54) METHODS OF PREVENTING OR TREATING MUCOSITIS BY ADMINISTERING RLIP76

(71) Applicant: TERAPIO CORPORATION, Austin, TX (US)

(72) Inventor: Casey C. Cunningham, Whitehouse, TX (US)

(73) Assignee: TERAPIO CORPORATION, Austin, TX (US)

( * ) Notice: Subject to any disclaimer, the term of this patent is extended or adjusted under 35 U.S.C. 154(b) by 0 days.

(21) Appl. No.: 15/021,924

(22) PCT Filed: Sep. 17, 2014

(86) PCT No.: PCT/US2014/056116
§ 371 (c)(1),
(2) Date: Mar. 14, 2016

(87) PCT Pub. No.: WO2015/042163
PCT Pub. Date: Mar. 26, 2015

(65) Prior Publication Data
US 2016/0228498 A1    Aug. 11, 2016

Related U.S. Application Data

(60) Provisional application No. 61/878,887, filed on Sep. 17, 2013.

(51) Int. Cl.
| *A61K 38/16* | (2006.01) |
| *A61K 9/127* | (2006.01) |
| *A61K 9/00* | (2006.01) |
| *A61K 47/32* | (2006.01) |
| *A61K 38/17* | (2006.01) |
| *A61K 45/06* | (2006.01) |
| *A61K 47/10* | (2017.01) |
| *A61K 47/24* | (2006.01) |

(52) U.S. Cl.
CPC .............. *A61K 38/16* (2013.01); *A61K 9/006* (2013.01); *A61K 9/127* (2013.01); *A61K 38/17* (2013.01); *A61K 45/06* (2013.01); *A61K 47/10* (2013.01); *A61K 47/24* (2013.01); *A61K 47/32* (2013.01)

(58) Field of Classification Search
CPC ........ A61K 38/16; A61K 47/10; A61K 45/06; A61K 47/24; A61K 38/17; A61K 47/32; A61K 9/006; A61K 9/127
See application file for complete search history.

(56) References Cited

U.S. PATENT DOCUMENTS

| 4,624,665 | A | 11/1986 | Nuwayser |
| 4,687,481 | A | 8/1987 | Nuwayser |
| 4,810,499 | A | 3/1989 | Nuwayser |
| 4,816,252 | A | 3/1989 | Stott et al. |
| 4,834,978 | A | 5/1989 | Nuwayser |
| 4,906,169 | A | 3/1990 | Chien et al. |
| 5,023,084 | A | 6/1991 | Chien et al. |
| 5,122,382 | A | 6/1992 | Gale et al. |
| 5,145,682 | A | 9/1992 | Chien et al. |
| 5,198,223 | A | 3/1993 | Gale et al. |
| 6,020,198 | A | 2/2000 | Bennett et al. |
| 6,750,015 | B2 | 6/2004 | Horwitz et al. |
| 7,611,839 | B2 | 11/2009 | Twine et al. |
| 8,163,692 | B2 | 4/2012 | Awasthi et al. |
| 8,486,410 | B2 | 7/2013 | Awasthi et al. |
| 8,586,553 | B2 | 11/2013 | Awasthi et al. |
| 9,211,260 | B2 | 12/2015 | Saddar et al. |
| 9,211,339 | B2 | 12/2015 | Cunningham |
| 2002/0119156 | A1 | 8/2002 | Chen et al. |
| 2003/0138793 | A1 | 7/2003 | Su et al. |
| 2004/0156853 | A1 | 8/2004 | Awasthi et al. |
| 2005/0123594 | A1 | 6/2005 | Awasthi et al. |
| 2005/0208054 | A1 | 9/2005 | Czech et al. |
| 2006/0030536 | A1 | 2/2006 | Yu et al. |
| 2006/0104982 | A1 | 5/2006 | Awasthi et al. |
| 2006/0104983 | A1 | 5/2006 | Awasthi et al. |
| 2006/0182749 | A1 | 8/2006 | Awasthi et al. |
| 2008/0279919 | A1 | 11/2008 | Awasthi et al. |
| 2010/0124566 | A1 | 5/2010 | Awasthi et al. |
| 2011/0020432 | A1 | 1/2011 | Cunningham |
| 2011/0020433 | A1 | 1/2011 | Cunningham |
| 2014/0294929 | A1 | 10/2014 | Cunningham |
| 2015/0024030 | A1 | 1/2015 | Awasthi et al. |

FOREIGN PATENT DOCUMENTS

| EP | 3046544 A1 | 7/2016 |
| JP | 2013500264 A | 1/2013 |
| WO | 0187266 A1 | 11/2001 |
| WO | 2005027939 A1 | 3/2005 |

(Continued)

OTHER PUBLICATIONS

Terapio Corporation—"RLIP76-PL Shows to Effectively Treat Animals Exposed to Lethal Levels of Radiation". 2 pages. Jan. 28, 2013.*
Ali et al., "Role of Anserine and/or Zinc in Modulating Nucleic Acid and Protein Disorders in rats Exposed to Gamma Irradiation," Journal of Pharmacology and Toxicology, 2007, vol. 2, No. 1, pp. 1-19.
"American Type Culture Collection", Tumor Cell lines, 2001, pp. 1-12.

(Continued)

*Primary Examiner* — Robert Landsman

(74) *Attorney, Agent, or Firm* — Kilpatrick Townsend & Stockton LLP

(57) ABSTRACT

Provided are compositions and methods for preventing or treating damage to mucosal tissue, for example as a result of radiation and/or chemotherapy. The damage may be, for example, oral or gastrointestinal mucositis.

34 Claims, 5 Drawing Sheets

(56) References Cited

FOREIGN PATENT DOCUMENTS

| WO | 2007102735 A1 | 9/2007 |
|---|---|---|
| WO | 2007127439 A1 | 11/2007 |
| WO | 2009100446 A1 | 8/2009 |
| WO | 2011011713 A1 | 1/2011 |
| WO | 2013/059736 A1 | 4/2013 |
| WO | 2015042163 A9 | 3/2015 |
| WO | 2015042163 A1 | 12/2015 |

OTHER PUBLICATIONS

Awasthi et al., "Transport functions and physiological significance of 76 kDa Ral-binding GTPase activating protein (RLIP76)," Acta Biochimica Polonica, 2002, vol. 49, No. 9, pp. 855-867.
Awasthi, "Role of 4-hydroxynonenal in stress-mediated apoptosis signaling," Mol. Aspects Med., 2003, vol. 24, pp. 219-230.
Awasthi et al., "A Novel Mechanism of Drug Resistance in Epilepsy", Blood Brain Barrier Conference at Cleveland Clinic Foundation, Cleveland, OH, Nov. 2-3, 2004, (Abstract).
Awasthi et al., "Anti-RLIP76 Antibodies Induce Apoptosis and Enhance Doxorubicin Cytotoxicity in Lung Cancer Cells", American Association for Cancer Research, 92nd Annual Meeting, New Orleans, LA, Proceedings: 42, Mar. 24-28, 2001, (Abstract 1507).
Awasthi et al., "Anti-RLIP76 Antibodies Induce Apoptosis in Lung Cancer Cells and Display Marked Synergy with Doxorubicin", American Association for Cancer Research, 93rd Annual Meeting, San Francisco, CA; Proceedings: 43, Apr. 6-10, 2002, (Abstract 4717).
Awasthi et al., "ATP-Dependent Colchicine Transport by Human Erythrocyte Glutathione Conjugate Transporter", Toxicology and Applied Pharmacology, vol. 155, Issue 3, 1999, pp. 215-226.
Awasthi et al., "ATP-Dependent Human Erythrocyte Glutathione-Conjugate Transporter. I. Purification, Photoaffinity Labeling, and Kinetic Characteristics of ATPase Activity", Biochemistry, vol. 37, Issue 15, 1998, pp. 5231-5238.
Awasthi et al., "ATP-Dependent Human Erythrocyte Glutathione-Conjugate Transporter. II. Functional Reconstitution of Transport Activity", Biochemistry, vol. 37, Issue 15, 1998, pp. 5239-5248.
Awasthi et al., "Functional Reassembly of ATP-Dependent Xenobiotic Transport by the N- and C-Terminal Domains of RLIP76 and Identification of ATP Binding Sequences", Biochemistry, vol. 40, Issue 13, 2001, pp. 4159-4168.
Awasthi et al., "Novel Function of Human RLIP76: ATP-Dependent Transport of Glutathione Conjugates and Doxorubicin", Biochemistry, vol. 39, Issue 31, 2000, pp. 9327-9334.
Awasthi et al., "RALPB1 is a major determinant of radiation sensitivity and glutathione-Conjugate transport", American Association for Cancer Research, 95th Annual Meeting, Orlando, FL, Mar. 27-31, 2004, (Abstract).
Awasthi et al., "RLIP76 and Cancer", Clinical Cancer Research, vol. 14, No. 14, 2008, pp. 4372-4377.
Awasthi et al., "RLIP76 Mediates Doxorubicin Transport and Resistance in Lung Cancer", 18th Annual Meeting of the International Society for Biological Therapy of Cancer (ISBTCI) Bethesda, MD, Oct. 30-Nov. 2, 2003, (Abstract).
Awasthi et al., "RLIP76, a non-ABC transporter, and drug resistance in epilepsy", BMC Neuroscience, vol. 6, 2005, pp. 61-71.
Awasthi et al., "RLIP76, a Novel Transporter Catalyzing ATP-Dependent Efflux of Xenobiotics", Drug Metabolism and Disposition, vol. 30, Issue 12, 2002, pp. 1300-1310.
Awasthi et al., "RLIP76 Is a Major Determinant of Radiation Sensitivity", Cancer Res., vol. 65, No. 14, 2005, pp. 6022-6028.
Awasthi et al., "Role of RLIP76 in lung cancer doxorubicin resistance: II. Doxorubicin transport in lung cancer by RLIP76", International Journal of Oncology, vol. 22, No. 4, 2003, pp. 713-720.
Awasthi et al., "Role of RLIP76 in lung cancer doxorubicin resistance: ILL. Anti-RLIP76 antibodies trigger apoptosis in lung cancer cells and synergistically increase doxorubicin cytotoxicity", International Journal of Oncology, vol. 22, No. 4, 2003, pp. 721-732.
Awasthi et al., "Targeting Multiple Signaling Pathways with RLIP76, Gordon Conference on Molecular Therapeutics of Cancer", Colby Sawyer College, New London New Hampshire, Jul. 20, 2005, (Abstract).
Awasthi et al., "Transport of glutathione conjugates and chemotherapeutic drugs by RLIP76 (RALBP1): A novel link between G-protein and tyrosine kinase signaling and drug resistance", International Journal of Cancer, vol. 106, Issue 5, 2003, pp. 635-646.
Awasthi et al., "Tyrphostin and Genistein Inhibit ATPase and transport activity of RLIP76 and increase doxorubicin toxicity in lung cancer cells", American Association of Cancer Research, 94th Annual Meeting, Washington, D.C., Jul. 11-14, 2003, (Abstract).
Baglia et al., "A Binding Site for Thrombin in the Apple 1 Domain of Factor XI", The Journal of Biological Chemistry, vol. 271, No. 7, 1996, pp. 3652-3658.
Bellm et al., "Patient reports of complications of bone marrow transplantation," Supp. Care Oncol., 2000, vol. 8, pp. 33-39.
Benedetti, "Identification of 4HNE as a cytotoxic product originating from the peroxidation of liver microsomal lipids," Biochem. Biophys. Acta., 1980, vol. 620, pp. 281-296.
Bezinelli, "Cost-effectiveness of the introduction of specialized oral care with laser therapy in hematopoietic stem cell transplantation," Hematol. Oncol., 2014, vol. 32, No. 1, pp. 31-39.
Black et al., "Effects of Dietary Constituents on Ultraviolet Light-mediated Carcinogenesis", Cancer Research, vol. 38, No. 5, May 1978, pp. 1384-1387.
Brizel et al., "Phase III randomized trial of amifostine as a radioprotector in head and neck cancer," J. Clin. Oncol., 2000, vol. 18, No. 19, pp. 3339-3345.
Brown, "Clinical consequences of oral mucositis," Seminars in Oncology Nursing, 2004, vol. 20, pp. 16-21.
Burroughs et al., "Discriminating self from nonself with short peptides from large proteomes," Immunogenetics, 2004, vol. 56, pp. 311-320.
Cella et al., "Evaluation of pain associated with oral mucositis during acute period after administration of high-dose chemotherapy," Cancer, 2003, vol. 98, No. 1, pp. 406-412.
Chaimberg et al., "Mucositis and airway obstruction in a pediatric patient," Anesthesia and Analgesia, 2004, vol. 99, No. 1, pp. 59-61.
Cheng et al., "Accelerated Metabolism and Exclusion of 4-Hydroxynonenal through Induction of RLIP76 and hGST5.8 is an Early Adaptive Response of Cells to Heat and Oxidative Stress", The Journal of Biological Chemistry, vol. 276, No. 44, 2001, pp. 41213-41223.
Dainiak, "Hematologic consequences of exposure to ionizing radiation", Experimental Hematology, vol. 30, No. 6, 2002, pp. 513-528.
Dermer et al., "Another Anniversary for the War on Cancer", Biotechnology vol. 12, No. 3, 1994.
Devi, "siRNA-based approaches in cancer therapy", Cancer Gene Therapy, vol. 13, No. 9, 2006, pp. 819-829.
Drake, "RALBP1 in Stress Resistance", The University of Texas at Arlington, Thesis, Dec. 2007, pp. 1-120.
Elting et al., "Risk, outcomes, and costs of radiation-induced oral mucositis among patients with head- and -neck malignancies," Int. J. Rad. Oncol. Biol. Phys., 2007, pp. 28-31.
Elting et al., "The burdens of cancer therapy, clinical and economic outcomes of chemotherapy-induced mucositis," Cancer, 2003, vol. 98, No. 7, pp. 1531-1539.
Esterbauer, "Chemistry and Biochemistry of 4-HNE, malondialdehyde, and related aldehydes," Free Rad. Biol. Med., 1991, vol. 11, pp. 81-128.
Freshney, "Culture of Animal Cells", A Manual of Basic Technique, 1983, pp. 3-4.
Hammond et al., "Functional Reconstitution of Pharmacologically Distinct Subtypes of Nucleoside Transporters in Liposomal Membranes," Journal of Pharmacology and Experimental Therapeutics, 1994, vol. 271, No. 2, pp. 906-917.
Hanly et al., "Review of Polyclonal Antibody Production Procedures in Mammals and Poultry," ILAR Journal, 1995, vol. 37, No. 3, pp. 93-115.
Iyer et al., "Effects of ionizing radiation in targeted and nontargeted cells", Archives of Biochemistry and Biophysics, vol. 376, No. 1, 2000, pp. 14-25.

(56) References Cited

OTHER PUBLICATIONS

Johnstone et al., Immunochemistry in Practice, 2nd Ed., Blackwell Scientific Publications, 1987, pp. 49-50.
Jones et al., "Epidemiology of treatment-associated mucosal injury after treatment with newer regiments for lymphoma, breast, lung, or colorectal cancer," Supp. Care Cancer, 2006, vol. 14, No. 6, pp. 505-515.
Keefe et al., "Updated clinical practice guidelines for the prevention and treatment of mucositis," Cancer, 2007, vol. 109, No. 5, pp. 820-831.
Kumar et al., "Gene manipulation through the use of small interfering RNA (siRNA): from in vitro to in vivo applications", Advanced Drug Delivery Reviews, vol. 59 (2-3), 2007, pp. 87-100.
Lalla, "Management of Oral Mucositis in Patients with Cancer," Nor. Am. Dent. Clin., 2009, vol. 52, No. 1, 17 pages.
Leenaars et al., "The Production of Polyclonal Antibodies in Laboratory Animals", ATLA, vol. 27, 1999, pp. 79-102.
Li et al., Chinese Pharmaceutical Journal, vol. 40, No. 19, 2005, pp. 1444-1448.
Logan et al., "Nuclear factor NF-kappaB and cyclo-oxygenase-2 expression in the oral mucosa following cancer chemotherapy," Oral Oncol., 2007, vol. 43, No. 4, pp. 395-401.
Mani et al., "Demonstrations of Equilibrative Nucleoside Transporters (hENT1 and hENT2) in Nuclear Envelopes of Cultured Human Choriocarcinoma (BeWo) Cells by Functional Reconstitution in Proteoliposomes," Journal of Biological Chemistry, 1998, vol. 273, No. 46, pp. 30818-30825.
Margutti et al., "Autoantibodies to the C-terminal subunit of RLIP76 induce oxidative stress and endothelial cell apoptosis in immune-mediated vascular diseases and atherosclerosis", Blood, vol. 111, No. 9, Nov. 2007, pp. 4559-4570.
Merriam-Webster online dictionary "prevent," pp. 1-3, printed Dec. 17, 2013.
Murphy, "Clinical and economic consequences of mucositis induced by chemotherapy and/or radiation therapy," J. Support Oncol., 2007, vol. 5, No. 9, pp. 13-21.
Naidu et al., "Chemotherapy-induced and/or radiation therapy-induced oral mucositis—complicating the treatment of cancer," Neoplasia, 2004, vol. 6, No. 5, pp. 423-431.
Negre-Salvayre et al., "Advanced lipid peroxidation end products in oxidative damage to proteins: potential role in diseases and therapeutic prospects for the inhibitors," Brit. J. Pharm., 2010, vol. 153, pp. 6-20.
Nonzee et al., "Evaluating the supportive care costs of severe radiochemotherapy-induced mucositis and pharyngitis," Cancer, 2008, vol. 113, No. 6, pp. 1446-1452.
PCT/US2014/056116, "International Preliminary Report on Patentability", Mar. 31, 2016, 7 pages.
PCT/US2014/056116, "International Search Report and Written Opinion", Nov. 27, 2014, 9 pages.
Peterson, "New frontiers in mucositis.," Am. Soc. Clin. Oncol. Educ. Book, 2012, vol. 32, pp. 545-551.
Peterson, "Novel Therapies," Semin. Oncol. Nurs., 2004, vol. 20, No. 1, pp. 53-58.
Peterson et al., "Randomized, placebo-controlled trial of Saforis for prevention and treatment of oral mucositis in breast cancer patients receiving anthracycline-based chemotherapy," Cancer, 2007, vol. 109, No. 2, pp. 322-331.
Pico et al., "Mucositis: its occurrence, consequences, and treatment in the oncology setting," The Oncologist, 1998, vol. 3, pp. 446-451.
Poli, "4-Hydroxynonenal-protein adducts: A reliable biomarker of lipid oxidation in liver disease," Mol. Asp. Me., 2007, vol. 29, pp. 69-71.
Ponnappa et al., "In vivo delivery of antisense oligonucleotides in pH-sensitive liposomes inhibits lipopolysaccharide-induced production of tumor necrosis factor-α in rats", Journal of Pharmacology and Experimental Therapeutics, vol. 297, 2001, pp. 1129-1136.
Popescu, "Adjuvant or palliative chemotherapy for colorectal cancer in patients 70 years or older," J. Clin. Oncol., 1999, vol. 17, pp. 2412-2418.
Pourreau-Schneider, "Soft-laser therapy for iatrogenic mucositis in cancer patients receiving high-dose fluroruacil: a preliminary report," J. Natl. Cancer Inst., 1992, vol. 84, No. 5, pp. 358-359.
Princeton.edu, "Biological Effects of Ionizing Radiation", Open Source Radiation Safety Training. Module 3: Biological Effects.
Rosen et al., "Palifermin reduces the incidence of oral mucositis in patients with metastatic colorectal cancer treated with fluorouracil-based chemotherapy," J. Clin. Oncol., 2006, vol. 24, No. 33, pp. 5194-5200.
Rubenstein et al., "Clinical practice guidelines for the prevention and treatment of cancer therapy-induced oral and gastrointestinal mucositis," Cancer, 2004, vol. 100, pp. 2026-2046.
Rutgers "Factsheet," Environmental Sciences Training Center, 1996, section 3; 3 pages.
Sandoval et al., "Management of chemo- and radiotherapy induced oral mucositis with low-energy laser: initial results of AC Camargo Hospital," J. Appl. Oral. Sci., 2003, vol. 11, No. 4, pp. 337-341.
Sause, "The Role of Radiotherapy in Non-Small Cell Lung Cancer", Chest, vol. 116 (Supplement), Issue 3, 1999, pp. 504S-508S.
Scully, "Oral health care for the cancer patient," Eur. J. Cancer B. Oral Oncol., 1996, vol. 32, No. 5, pp. 281-292.
Sennhenn-Kirchner et al., "Dental therapy before and after radiotherapy—an evaluation on patients with head and neck malignancies," Clin. Oral. Investig., 2009, vol. 13, No. 2, pp. 157-164.
Sharma, "4-Hydroxynonenal self-limits Fas-mediated DISC independent apoptosis by promoting export Daxx from nucleus to cytosol and its binding to Fas," Biochem., 2008, vol. 47, pp. 143-156.
Sharma et al., "RLIP76 (RALBP1)-mediated transport of leukotriene C4 (LTC4) in cancer cells: Implications in drug resistance", International Journal of Cancer, vol. 112, Issue 6, 2004, pp. 934-942.
Sharma et al., "RLIP76 Is the Major ATP-Dependent Transporter of Glutathione-Conjugates and Doxorubicin in Human Erythrocytes", Archives of Biochemistry and Biophysics, vol. 391, Issue 2, 2001, pp. 171-179.
Singhal et al., "Regression of melanoma in a murine model by RLIP76 depletion," Cancer Research, vol. 66, No. 4, 2006, pp. 2354-2360.
Singhal et al., "Depletion of RLIP76 sensitizes lung cancer cells to doxorubicin", Biochemical Pharmacology, vol. 70, No. 3, 2005, pp. 481-488.
Singhal et al., "Purification and functional reconstitution of intact ral-binding GTPase activating protein, RLIP76, in artificial liposomes", ACTA Biochimica Polonica, vol. 48, No. 2, 2001, pp. 551-562.
Singhal et al., "Regression of lung and colon cancer xenografts by depleting or inhibiting RLIP76 (Ral-binding protein 1)", Cancer Research, vol. 67, 2007, pp. 4382-4389.
Singhal et al., "Regression of prostate cancer xenografts by RLIP76 depletion", Biochem. Pharmacol., vol. 77, No. 6, 2009, pp. 1074-1083.
Singhal et al., "RLIP76 in defense of radiation poisoning", International Journal of Radiation Oncology Biology Physics, vol. 72, No. 2, 2008, pp. 553-561.
Singhal et al., "Role of RLIP76 in lung cancer doxorubicin resistance: I. The ATPase activity of RLIP76 correlates with doxorubicin and 4-hydroxynonenal resistance in lung cancer cells", International Journal of Oncology, vol. 22, No. 2, 2003, pp. 365-375.
Singhal et al., "The role of PKCα and RLIP76 in transport-mediated doxorubicin-resistance in lung cancer", FEBS Letters, vol. 579, No. 30, 2005, pp. 4635-4641.
Sioud et al., "Cationic liposome-mediated delivery of siRNAs in adult mice", Biocehmical and Biophysical Research Communications, vol. 312, No. 4, 2003, pp. 1220-1225.
Sonis, "New thoughts on the initiation of mucositis," Oral Diseases, 2010, vol. 16, pp. 597-600.
Sonis, "Oral mucositis and the clinical and economic outcomes of hematopoietic stem-cell transplantation," J. Clin. Oncol., 2001, vol. 19, No. 8, pp. 2201-2205.
Sonis, "Oral Mucositis," Anticancer Drugs, 2011, vol. 22, No. 7, pp. 607-612.

(56) References Cited

OTHER PUBLICATIONS

Sonis et al., "Perspectives on cancer therapy-induced mucosal injury: pathogenesis, measurement, epidemiology, and consequences for patients," Cancer, 2004, vol. 1, No. 100, pp. 1995-2025.
Soranzo et al., "Lack of Support for a Role of RLIP76 (RALBP1) in Response to Treatment or Predisposition to Epilepsy", Epilepsia, vol. 48, No. 4, 2007, pp. 674-683.
Stuckler et al., "RLIP76 Transports Vinorelbine and Mediates Drug Resistance in Non-Small Cell Lung Cancer", Cancer Research, vol. 65, No. 31, 2005, pp. 991-998.
Treister, "Mucositis: biology and management," Curr. Opin. Otolaryn. Head Neck Surg., 2007, vol. 15, No. 2, pp. 123-129.
Trotti, "Common toxicity criteria: version 2.0. An improved reference for grading the acute effects of cancer treatment: impact on radiotherapy," Intl. J. Radiat. Oncol. Biol. Phys., 2000, vol. 47, pp. 13-47.
Trotti, "Mucositis incidence, severity and associated outcomes in patients with head and neck cancer receiving radiotherapy with or without chemotherapy: a systematic literature review," Radiother. Oncol., 2003, vol. 66, No. 3, pp. 253-262.
"Ultraviolet Radiation Guide," Navy Environmental Health Center, Apr. 1992, 21 pages.
U.S. NRC Fact Sheet "Biological Effects of Radiation", Dec. 2004, pp. 1-9.
USNRC Technical Training Center, "Natural and Man-Made Radiation Sources," Reactor Concepts Manual, Feb. 2001, pp. 6-1 to 6-12.
Vera-Llonch et al., "Oral Mucositis in patients undergoing radiation treatment for head and neck carcinoma," Cancer, 2006, vol. 106, No. 2, pp. 329-336.
Von Bultzingslowen, "Growth factors and cytokines in the prevention and treatment of oral and gastointestinal mucositis," Supp. Care Cancer, 2006, vol. 14, No. 6, pp. 519-527.
Wagner et al., "Treatment of radiation exposure and contamination", Radiographies vol. 14, No. 2, 1994, pp. 387-396.
Weiner, "An Overview of Monoclonal Antibody Therapy of Cancer", Seminars in Oncology, vol. 26, No. 4, Suppl. 12, 1999, pp. 41-50.
Wickramarachchi et al., "Identification of Membrane Anchoring Domains of RLIP76 Using Deletion Mutant Analysis", American Association of Cancer Research, 96th Annual Meeting Anaheim, CA, Apr. 16-20, 2005, (Abstract).
Wilkes, "Prevention and treatment of oral mucositis following cancer chemotherapy," Semin. Oncol., 1998, vol. 25, No. 5, pp. 538-551.
Wingard et al., "Infection and mucosal injury in cancer treatment," J. Natl. Cancer Insti. Monographs, 2001, vol. 29, pp. 31-36.
Wright, "Chemotherapy-induced oral mucositis: new approaches to prevention and management," Exp. Opin. Drug. Saf., 2005, vol. 4, pp. 193-200.
Xu et al., "Investigation of the oral infections and manifestations seen in patients with advanced cancer," Pak. J. Med. Sci., 2013, vol. 29, No. 5, pp. 1112-1115.
Yadav et al., "Identification of Membrane-Anchoring Domains of RLIP76 Using Deletion Mutant Analyses", Biochemistry, vol. 43, 2004, pp. 16243-16253.
Yadav et al., "POB1 over-expression inhibits RLIP76-mediated transport of glutathione-conjugates, drugs and promotes apoptosis", Biochemical Research Communications, vol. 328, 2005, pp. 1003-1009.
Yang et al., "Role of Glutathione S-Transferases in Protection against Lipid Peroxidation: Overexpression of hGSTA2-2 in K562 Cells Protects Against Hydrogen Peroxide-Induced Apoptosis and Inhibits JNK and Caspase 3 Activation", Journal of Biological Chemistry, vol. 276, No. 22, 2001, pp. 19220-19230.
Brizel et al., Journal of Clinical Oncology, vol. 18, No. 24 Dec. 15, 2000: pp. 4110-4111 (Correction of "Phase III Randomized Trial of Amifostine as a Radioprotector in Head and Neck Cancer" (J Clin Oncol 18:3339-3345, 2000)). The Commercialization plan cites the corrected appendices.
Extended European Search Report issued on Feb. 16, 2017, in European application No. 14846118.9, 7 pages.

\* cited by examiner ated in the receiver compartment over the sampling period, compared to the other formulations. RLIP76-PL/CMC, RLIP76-PL/SGDC, and RLIP76-PL/PAA were only slightly detectable in the receiver compartment beginning at 180 minutes.

SEQUENCE LISTING

```
<160> NUMBER OF SEQ ID NOS: 1

<210> SEQ ID NO 1
<211> LENGTH: 655
<212> TYPE: PRT
<213> ORGANISM: homo sapiens

<400> SEQUENCE: 1

Met Thr Glu Cys Phe Leu Pro Pro Thr Ser Ser Pro Ser Glu His Arg
1               5                   10                  15

Arg Val Glu His Gly Ser Gly Leu Thr Arg Thr Pro Ser Ser Glu Glu
                20                  25                  30

Ile Ser Pro Thr Lys Phe Pro Gly Leu Tyr Arg Thr Gly Glu Pro Ser
            35                  40                  45

Pro Pro His Asp Ile Leu His Glu Pro Pro Asp Val Val Ser Asp Asp
        50                  55                  60

Glu Lys Asp His Gly Lys Lys Lys Gly Lys Phe Lys Lys Lys Glu Lys
65                  70                  75                  80

Arg Thr Glu Gly Tyr Ala Ala Phe Gln Glu Asp Ser Ser Gly Asp Glu
                85                  90                  95

Ala Glu Ser Pro Ser Lys Met Lys Arg Ser Lys Gly Ile His Val Phe
            100                 105                 110

Lys Lys Pro Ser Phe Ser Lys Lys Lys Glu Lys Asp Phe Lys Ile Lys
        115                 120                 125

Glu Lys Pro Lys Glu Glu Lys His Lys Glu Glu Lys His Lys Glu Glu
    130                 135                 140

Lys His Lys Glu Lys Lys Ser Lys Asp Leu Thr Ala Ala Asp Val Val
145                 150                 155                 160

Lys Gln Trp Lys Glu Lys Lys Lys Lys Lys Pro Ile Gln Glu Pro
```

```
                165                 170                 175
Glu Val Pro Gln Ile Asp Val Pro Asn Leu Lys Pro Ile Phe Gly Ile
            180                 185                 190

Pro Leu Ala Asp Ala Val Glu Arg Thr Met Met Tyr Asp Gly Ile Arg
            195                 200                 205

Leu Pro Ala Val Phe Arg Glu Cys Ile Asp Tyr Val Glu Lys Tyr Gly
210                 215                 220

Met Lys Cys Glu Gly Ile Tyr Arg Val Ser Gly Ile Lys Ser Lys Val
225                 230                 235                 240

Asp Glu Leu Lys Ala Ala Tyr Asp Arg Glu Glu Ser Thr Asn Leu Glu
            245                 250                 255

Asp Tyr Glu Pro Asn Thr Val Ala Ser Leu Leu Lys Gln Tyr Leu Arg
            260                 265                 270

Asp Leu Pro Glu Asn Leu Leu Thr Lys Glu Leu Met Pro Arg Phe Glu
            275                 280                 285

Glu Ala Cys Gly Arg Thr Thr Glu Thr Glu Lys Val Gln Glu Phe Gln
            290                 295                 300

Arg Leu Leu Lys Glu Leu Pro Glu Cys Asn Tyr Leu Leu Ile Ser Trp
305                 310                 315                 320

Leu Ile Val His Met Asp His Val Ile Ala Lys Glu Leu Glu Thr Lys
                325                 330                 335

Met Asn Ile Gln Asn Ile Ser Ile Val Leu Ser Pro Thr Val Gln Ile
            340                 345                 350

Ser Asn Arg Val Leu Tyr Val Phe Phe Thr His Val Gln Glu Leu Phe
            355                 360                 365

Gly Asn Val Val Leu Lys Gln Val Met Lys Pro Leu Arg Trp Ser Asn
            370                 375                 380

Met Ala Thr Met Pro Thr Leu Pro Glu Thr Gln Ala Gly Ile Lys Glu
385                 390                 395                 400

Glu Ile Arg Arg Gln Glu Phe Leu Leu Asn Cys Leu His Arg Asp Leu
            405                 410                 415

Gln Gly Gly Ile Lys Asp Leu Ser Lys Glu Glu Arg Leu Trp Glu Val
            420                 425                 430

Gln Arg Ile Leu Thr Ala Leu Lys Arg Lys Leu Arg Glu Ala Lys Arg
            435                 440                 445

Gln Glu Cys Glu Thr Lys Ile Ala Gln Glu Ile Ala Ser Leu Ser Lys
            450                 455                 460

Glu Asp Val Ser Lys Glu Glu Met Asn Glu Asn Glu Glu Val Ile Asn
465                 470                 475                 480

Ile Leu Leu Ala Gln Glu Asn Glu Ile Leu Thr Glu Gln Glu Glu Leu
            485                 490                 495

Leu Ala Met Glu Gln Phe Leu Arg Arg Gln Ile Ala Ser Glu Lys Glu
            500                 505                 510

Glu Ile Glu Arg Leu Arg Ala Glu Ile Ala Glu Ile Gln Ser Arg Gln
            515                 520                 525

Gln His Gly Arg Ser Glu Thr Glu Glu Tyr Ser Ser Glu Ser Glu Ser
            530                 535                 540

Glu Ser Glu Asp Glu Glu Leu Gln Ile Ile Leu Glu Asp Leu Gln
545                 550                 555                 560

Arg Gln Asn Glu Glu Leu Glu Ile Lys Asn Asn His Leu Asn Gln Ala
            565                 570                 575

Ile His Glu Glu Arg Glu Ala Ile Ile Glu Leu Arg Val Gln Leu Arg
            580                 585                 590
```

-continued

```
Leu Leu Gln Met Gln Arg Ala Lys Ala Glu Gln Gln Ala Gln Glu Asp
        595                 600                 605

Glu Glu Pro Glu Trp Arg Gly Gly Ala Val Gln Pro Pro Arg Asp Gly
    610                 615                 620

Val Leu Glu Pro Lys Ala Ala Lys Glu Gln Pro Lys Ala Gly Lys Glu
625                 630                 635                 640

Pro Ala Lys Pro Ser Pro Ser Arg Asp Arg Lys Glu Thr Ser Ile
                645                 650                 655
```

METHODS OF PREVENTING OR TREATING MUCOSITIS BY ADMINISTERING RLIP76

CROSS-REFERENCE TO RELATED APPLICATIONS

This application is a national phase application of PCT Application No. PCT/US14/56116 filed Sep. 17, 2014, which claims the benefit of U.S. Provisional Patent Application Ser. No. 61/878,887, filed on Sep. 17, 2013, which is incorporated by reference herein in its entirety.

BACKGROUND

Mucositis is a condition characterized by swelling, irritation, and discomfort of mucosal linings such as those of the gastrointestinal tract and the oral and oral pharyngeal cavities, and can result in mouth and throat sores, diarrhea, abdominal cramping and tenderness, and rectal ulcerations. This condition occurs in approximately half of all cancer subjects, and is a common side effect of cancer treatments involving radiation and/or chemotherapy. The goal of these approaches to cancer treatment is to kill rapidly dividing cancer cells but, unfortunately, other rapidly dividing cells are killed by the treatment as well, including cells that line regions such as the gastrointestinal tract, leading to mucositis. Symptoms of mucositis generally occur five to ten days after the start of cancer treatment and can take two to four weeks after cessation of treatment to clear. The incidence of mucositis, as well as its severity, depends on factors such as the type and duration of the cancer treatment. It is also highly prevalent in subjects treated with high dose chemotherapy and/or irradiation for the purpose of myeloablation, in preparation for stem cell or bone marrow transplantation.

Mucositis adversely impacts the quality of life of cancer subjects in several ways. For example, the mouth and throat sores of mucositis can cause significant pain and make it difficult to eat, drink, and even take oral medication. Mucositis is also accompanied by a severe risk of infection, as it can lead to a breach in the otherwise protective linings of the oral mucosa and gastrointestinal tract, which are colonized by a vast array of microorganisms. Further, efforts to counter the discomforts of mucositis can lead to disruptions in cancer treatment, alterations in treatment dosages, or shifting to different modes of treatment. Severe mucositis can also lead to the need for parenteral nutrition or hospitalization. The development of effective approaches to preventing and treating mucositis is therefore important for improving the care of cancer subjects.

Overall, mucositis affects 15-40 percent of subjects receiving standard-dose chemotherapy and 76-100 percent of subjects receiving higher doses of chemotherapy for bone marrow transplantation. Mucositis also affects virtually all subjects receiving radiation therapy for head and neck cancer, as well as subjects receiving radiation along the GI tract. For example, esophagitis (or esophageal mucositis) is a major complication of chemoradiation therapy in subjects with non-small cell lung cancer that produces significant morbidity and results in treatment interruptions. Mucositis afflicts over 400,000 subjects a year in the US, and the incidence is growing as the need for radiation and chemotherapy treatments grows. This represents a potential annual market of greater than $800 million in the US.

Treatment of oral mucositis is a significant unmet medical need. Current treatment strategies are primarily palliative and include mucosal coating mixtures that may contain topical anesthetics and antibiotics to prevent infection. These treatments provide little benefit, and do not speed healing or decrease severity of mucositis.

SUMMARY

Provided herein are methods for preventing or treating mucositis comprising administering to the subject a composition comprising RLIP76 or a fragment thereof. Also provided are methods of reducing the severity of mucositis in a subject. The method includes the steps of administering to the subject a composition comprising an effective amount of RLIP76.

Provided are methods to reduce or delay the onset of mucositis comprising administering a composition comprising RLIP76 or a fragment thereof and a pharmaceutically acceptable carrier, wherein the RLIP76 or fragment thereof delays the onset, or reduces the intensity or duration of mucositis.

DETAILED DESCRIPTION

Figure 1:
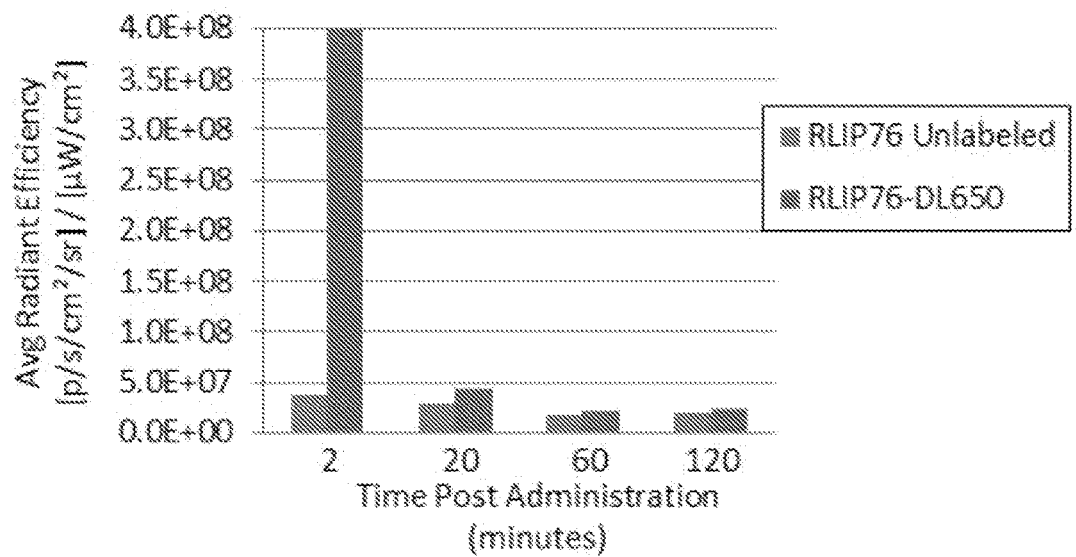
FIG. 1 is a graph showing RLIP76 retention in the oral mucosa after topical administration to the cheek.

As described herein, RLIP76 can be used to prevent and/or treat damage to mucosal tissue, and in particular to prevent and/or treat mucositis. Such methods include reducing the severity of mucositis in the subject and comprise administering to the subject a composition comprising RLIP76. Optionally, the mucositis is caused by radiation exposure or chemical exposure. Optionally, the mucositis is caused by exposure to a chemotherapeutic agent.

Mucositis is an inflammatory and ulcerative injury of the mouth, throat or GI tract most commonly caused by chemotherapy or radiation therapy for cancer. This disease has its onset when chemotherapy or radiation disrupts the mucosal surface of the mouth and other portions of the GI tract, affecting both the epithelial layer and the underlying connective tissue. In severe cases, oral mucositis can be extremely painful, preventing the subject from eating, and requiring hospitalization for hydration, narcotics for pain, and/or total parenteral nutrition. Pain resulting from mucositis is so severe that it is often cited by cancer subjects as the primary reason for discontinuing treatment. Subjects suffering from mucositis may feel as if they were drinking scalding hot water and scraping the inside of their mouth with coarse sand paper followed by running their tongue over a cheese grater. Mucositis can also be life-threatening because oral ulcerations can permit the entry of bacteria into the bloodstream, a situation which can be fatal in a subject already immune-compromised by treatment for cancer.

Mucositis is a common toxicity associated with both chemical exposure (e.g., chemotherapy) and radiation. Mucositis is characterized by ulceration in the oro-esophageal and gastrointestinal mucosae that results in pain, dysphagia, diarrhea and dysfunction. Thus, the mucositis can be gastrointestinal mucositis or oral mucositis. The most visible form is oral mucositis which results in severe discomfort and impairs a patient's ability to eat, swallow and talk. Mucositis begins as oral redness about 4-5 days following chemotherapy infusion or at cumulative doses of head and neck radiation of about 10 Gy. Patients also often complain of burning and intolerance of spicy foods at this stage. Within 7 to 10 days after chemotherapy or at cumulative radiation doses of 30 Gy, ulcers develop, resulting in marked discomfort, often requiring opioid intervention and in many cases causing patients to alter their diet. Chemotherapy patients who also develop neutropenia are at significant risk of bacteraemia and sepsis from oral microorganisms resulting in increased days of fever, antibiotic use and hospitalization. Chemotherapy-induced mucositis lasts approximately 1 week and generally heals spontaneously by 21 days after infusion. Radiation-induced mucositis stays at a peak for at least 2 weeks following the completion of radiotherapy (typically 60-70 Gy). As a result, it is not uncommon for patients receiving radiotherapy for cancers of the mouth and contiguous areas to have severe ulcerative oral mucositis persisting for 5-7 weeks. Mucositis has an indirect effect on tumor outcomes as its presence often necessitates an unfavorable modification of anti-cancer therapy such as breaks in radiation treatment or a dose reduction of chemotherapy.

Approximately 450,000 patients per year will develop oral complications during chemotherapy in the US. Essentially identical numbers are found internationally because, although the total number of cancer patients is higher, treatment patterns differ from the US. Some degree of oral mucositis occurs in approximately 40% of patients who receive cancer chemotherapy. Over 50% of patients being treated with fluorouracil, adriamycin and cytoxan (FAC) for node-positive breast cancer develop mucositis. 15-20% of patients being treated with the most common chemotherapy regimens for colorectal cancer develop mucositis. The incidence of mucositis is higher in patients who receive continuous infusion therapy for breast and colon cancer and in those who receive adjuvant therapy for head and neck tumors. At least 75% of patients who receive myeloablative conditioning regimens (chemotherapy with or without total body irradiation) in preparation for hematopoietic stem cell transplant (HSCT) develop oral mucositis. Mucositis is the most common symptom and distressing complication of HSCT. 30-50% of patients with HSCT complain that mucositis is their most significant toxicity. Combining different chemotherapeutic drugs further intensifies the likelihood of mucositis: from 40% to 70% of patients treated with standard chemotherapy regimens suffer mucositis.

Radiation-induced mucositis occurs in almost all patients who are treated for cancers of the mouth, oropharynx and nasopharynx (29,000 US patients in 2008), and in approximately two-thirds of those treated for cancers of the hypopharynx or larynx (13,000 in US in 2008). World-wide incidence exceeds 500,000 cases annually. Mucositis risk and severity are determined by the treatment dose, radiation field size and fractionation schedules prescribed for individual patients. Hyper-fractionated schedules and combination of radiation with chemotherapy increase the prevalence, severity and duration of mucositis.

The initiation phase of mucositis occurs quickly after radiation or chemotherapy and is followed by both DNA and non-DNA damage. Direct cellular injury targeting the basal epithelial cells occurs simultaneously with the generation of reactive oxygen species (ROS) such as superoxide. Primary damage responses, noted in the cells and tissues of the submucosa, then follows and is characterized by the expression of early response genes followed by production of a range of destructive proteins and molecules such as the pro-inflammatory cytokines [interleukin-1 (IL-1), interleukin-6 (IL-6) and tumor necrosis factor (TNF) alpha], nitric oxide (NO), ceramide and matrix metalloproteinases (MMPs) that lead to apoptosis and tissue injury.

Current treatment of mucositis (current guidelines) includes oral care or oral cryotherapy (ice) for patients receiving 5-FU or methotrexate. The only approved drug is palifermin and it is used only for patients undergoing HSCT.

Thus, provided are methods of preventing or treating mucositis by administering to a subject a composition comprising RLIP76. Optionally, the subject does not have but is at risk of developing mucositis. A subject is at risk of developing mucositis, as described above, based, for example, on an expected exposure, a concurrent exposure, or a recent exposure to a chemical agent (e.g., a chemotherapeutic agent) or to radiation. Development of mucositis is prevented in the subject by administration of the composition. The compositions can be administered prior to, concurrently with, or after a treatment that places the subject at risk of developing mucositis. Optionally, administration occurs prior to a treatment or exposure that places the subject at risk of developing mucositis. Optionally, administration occurs concurrently with a treatment or exposure that places the subject at risk of developing mucositis. Optionally, administration occurs after treatment that places the subject at risk of developing mucositis. The exposure that places the subject at risk of developing mucositis can be a therapeutic exposure such as radiation therapy or chemotherapy. Optionally, the radiation is selected from the group consisting of therapeutic radiation, x-ray radiation, gamma radiation, ultraviolet radiation and nuclear radiation.

RLIP76 (also known as RALBP1 or RIP1) is a ubiquitous protein found in Drosophila to humans that serves multiple roles in cellular physiology. When membrane-associated, the protein functions as a multi-specific efflux pump for a variety of compounds, including amphiphilic small molecules such as Vinca alkaloids and anthracylines, which are common anticancer drugs. However, RLIP76 transport also involves movement from the cell of endogenous glutathione electrophile conjugates (GS-E) formed from reactive oxygen species (ROS). ROS are produced by a variety of insults, such as radiation and a plethora of organic chemicals, and are toxic to the cell on many levels. As their name implies, ROS are highly reactive and bind to almost anything in their path, including proteins, lipids and nucleic acids, modifying each of these as they are contacted. The damage done by ROS to lipids (lipid peroxidation) is particularly pernicious since the resulting peroxidation products are themselves toxic. These include proapoptotic reactive alkenals, such as 4 hydroxynonenal (4-HNE), which are long lived and can accumulate in the cell, ultimately leading to further damage and death. As such, RLIP76 is an important component of stress response in cultured cells and provides protection from stressors including heat, oxidant chemicals, chemotherapeutic agents, UV irradiation and X-irradiation.

The normal cell has defense mechanisms designed to bind up (conjugate) these ROS-associated toxins, chief of which is glutathione. Glutathione binds electrophilic compounds to sequester the reactive electrons. However, the resulting conjugates (GS-E) are harmful or fatal to the cell if allowed to accumulate, and so must be removed by the cell. Although not wishing to be bound to any particular theory, it appears that the active efflux of GS-E derived from these toxic intermediates is the principal mechanism by which RLIP76 confers resistance to oxidant and radiant stressors.

The protective effect of RLIP76 goes beyond its protection of potentially toxic chemical substituents and their by-products. For example, electrophilic products of lipid peroxidase (LPO) caused by reactive oxygen species generated during radiation may partly account for cell killings by radiation. As detailed herein, RLIP76-mediated transport of GSH conjugates of these electrophiles provides protection from radiation. Such protection may be readily transferred to a larger scale to protect mammals against damaging radiation, including ionizing, electromagnetic, thermal, and laser radiation, wherein either long- or short-range electrons are involved.

Therefore, RLIP76 mediates transport of endogenously generated chemicals, metabolic products, their by-products and exogenously administered drugs or radiation, and their by-products. RLIP76 mediates the transport of most chemicals and by-products that also involve GS-E (e.g., conjugate of 4-HNE). For example, RLIP76-enriched cells are resistant to toxicity in the form of chemical toxicity (organic or inorganic) or from damage (e.g., from stress, oxidation, alkylation, radiation). The function of RLIP76 via an ATP-dependent efflux of xenobiotics (e.g., GS-E and exogenous and endogenous electrophiles). Here, xenobiotics, radiation, their metabolites, mitochondrial electron transport and metal ions generate ROS that can cause membrane lipid peroxidation and 4-hydroxynonenal (the toxic end product of lipid peroxidation), which can cause DNA damage leading to mutagenesis, carcinogenesis and apoptosis as well as modulate the stress mediated signaling pathways. RLIP76 mediates the ATP-dependent efflux of a wide variety of metabolic, stress, and pharmaceutical by-products, such as amphiphilic drugs, GSH-conjugates (GS-E) of both xeno and endo-biotics, GS-HNE and leukotrienes, from eukaryotic cells. The transport of GS-E is important for maintaining functionality of GSTs and glutathione reductase (GR), because these enzymes are inhibited by GS-E. RLIP76 regulates the intracellular concentrations of 4-HNE by a coordinated mechanism with cellular GSTs.

The RLIP76 protein may be divided into four regions out of which two central domains carry a Rac-1/CDC42 GAP activity and a Ral binding domain. Representative nucleotide sequences of human RLIP76 (GenBank Accession Number NM-006788) and mouse RLIP76 (NM-009067), and amino acid sequences of human RLIP76 (GenBank Accession Number NP-006779) and mouse RLIP76 (GenBank Accession Number NP-033093), have been described. The human RLIP76 amino acid sequence includes sites for N-glycosylation (amino acids 341-344), cAMP (amino acids 113-116), cGMP-dependent protein kinase phosphorylation (amino acids 650 653), tyrosine kinase phosphorylation (amino acids 308-315), N-myristolation (amino acids 21-26, 40-45, and 191-196), leucine zipper pattern (amino acids 547-578) and several protein kinase C phosphorylation, casein kinase II phosphorylation, trypsin and chymotrypsin cut sites. The presence of such motifs in the primary structure of RLIP76, and its facile proteolytic degradation, shows RLIP76 to be involved in several intra- and extracellular processes (e.g., protein processing, intracellular signaling, protein degradation, recognition, tagging, etc.) and that proteolytic processing of RLIP76 is required for the multiple functions. The peptide fragments of RLIP76 individually or in association with other fragments may catalyze these various functions. For example, N terminal and C-terminal fragments of RLIP76, fragments that are individually incapable of mediating ATP-dependent transport, can catalyze the transport of electrically charged drugs (e.g., DOX, colchicines) when reconstituted together in proteoliposomes.

Optionally, RLIP76 comprises a sequence of 655 amino acids as set forth in GenBank Accession Number NP-006779). Optionally, RLIP76 comprises a sequence as disclosed in US 2005/0123594, US 2006/0182749, US 2008/0279919, US 2010/0124566, or WO 2009/100446A1, the contents of which are incorporated by reference in their entireties. As used herein, RLIP76 is used as an example. Active fragments of RLIP76 or modified versions of RLIP76 can be used similarly.

Unlike the ABC transporters, no transmembrane alpha-helices are evident in the RLIP76 sequence. The association of RLIP76 with membranes has, however, been demonstrated by immunohistochemical studies using specific antibodies (Awasthi, et al., Proceedings of the American Association for Cancer Research, 43:Abst. 4717, 2002; herein incorporated by reference). The extraction of RLIP76 from cell lysates requires detergent, suggesting membrane association, a feature important for transport. These findings show a greater diversity in this transporter, in terms of structural elements defining ATP binding and mode of membrane insertion, than is currently accepted. In addition, the distinction between transporters for anions as opposed to neutral or cationic substrates is blunted because RLIP76 catalyzes the transport of both, and, in contrast to MRP 1, does so without co-transporting GSH.

RLIP76 expressed in cultured cells or in *E. coli* undergoes facile proteolysis during purification. The most prominent peptides, N-RLIP76 1-367 and C-RLIP76 410-655, arising from the N and C termini of RLIP76, respectively, appear as 49 kDa and 38 kDa bands in SDS-gels. Both these peptides display constitutive ATPase activity that may be stimulated in the presence of the anionic or cationic ligands transported by RLIP76. Both peptides bind ATP, as shown by photoaffinity labeling that increased in the presence of vanadate, indicating the trapping of a reaction intermediate in the ATP binding site. Neither of the two fragments catalyze transport when reconstituted alone in proteoliposomes. However, when reconstituted together, ATP dependent transport of charged chemicals (e.g., DNP-SG, DOX) is observed with kinetic parameters similar to those for RLIP76. The ATP binding sites in N-RLIP761-367 and C RLIP76410-655 were identified to be amino acids 69-74 and amino acids 418-425, respectively. Mutations of K74 and K425 in the N and C-terminal peptides, respectively, abrogate the ATPase activity, ATP binding capacity, and transport function. The sequence of these ATP binding sites is not identical to the consensus sequence for the P-loop (Walker motif).

In addition to the human RLIP76 nucleic acid sequence described above, a number of single nucleotide polymorphisms (SNPs) have been described in the art within the human RLIP76 gene, three of which (an A to G mutation at nucleotide 660 of the coding sequence, a G to A mutation at nucleotide 838 of the coding sequence, and a C to T mutation at nucleotide 2065 of the coding sequence) fall within the RLIP76 coding sequence. These nucleotide changes result in changing the amino acid sequence from lysine to glutamate at amino acid position 149, from arginine to glutamine at amino acid position 208, and from alanine to valine at amino acid position 617, respectively. These SNPs, along with SNPs that occur in the introns of the human RLIP76 gene, and well as SNPs that occur in the 5' and 3' untranslated regions of the human RLIP76 gene, are described in the Single Nucleotide Polymorphism (SNP) database on the National Center for Biotechnology Information web site.

As used throughout, when RLIP76 is referenced to refer to a full length RLIP76 amino acid sequence, it is understood that one or more fragments of RLIP76 amino acid sequence or mutants of the RLIP76 can be used instead. Optionally, the RLIP76 comprises SEQ ID NO:1, fragments thereof, or modified variants (e.g., conservatively modified variants that include one or more conservative amino acid substitutions) thereof. Optionally, RLIP76 can refer to an amino acid sequence that has about 99% identity or homology with the human RLIP76 amino acid sequence as shown in GenBank Accession Number NP-006779 or SEQ ID NO:1, about 98% identity or homology, about 95% identity or homology, about 90% identity or homology, about 85% identity or homology, or about 80% identity or homology to the human RLIP76 amino acid sequence as shown in GenBank Accession Number NP-006779 or SEQ ID NO:1. The percentage of sequence identity may reflect certain additions, deletions, substitutions, silent or conservative mutations to the sequences.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

It is understood that the nucleic acids that can encode those peptide, polypeptide, or protein sequences, variants and fragments thereof are also disclosed. This would include all degenerate sequences related to a specific polypeptide sequence, i.e., all nucleic acids having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every sequence is in fact disclosed and described herein through the disclosed polypeptide sequence.

As with all peptides, polypeptides, and proteins, including fragments thereof, it is understood that additional modifications in the amino acid sequence of the provided polypeptides can occur that do not alter the nature or function of the peptides, polypeptides, or proteins. Such modifications include, for example, conservative amino acids substitutions and are discussed in greater detail below.

Thus, the provided agents comprising polypeptides or nucleic acids can be further modified and varied so long as the desired function is maintained. It is understood that one way to define any known modifications and derivatives or those that might arise, of the disclosed nucleic acid sequences and proteins herein is through defining the modifications and derivatives in terms of identity to specific known sequences. Specifically disclosed are polypeptides which have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the polypeptides provided herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman, Adv. Appl. Math 2:482 (1981), by the identity alignment algorithm of Needleman and Wunsch, J. Mol Biol. 48: 443 (1970), by the search for similarity method of Pearson and Lipman, Proc. Natl. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-7710 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Protein modifications include amino acid sequence modifications. Modifications in amino acid sequence may arise naturally as allelic variations (e.g., due to genetic polymorphism), may arise due to environmental influence (e.g., exposure to ultraviolet light), or may be produced by human intervention (e.g., by mutagenesis of cloned DNA sequences), such as induced point, deletion, insertion, and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 1 and are referred to as conservative substitutions.

TABLE 1

Amino Acid Substitutions

| Amino Acid | Substitutions (others are known in the art) |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. By way of example, modifications are made by site specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Provided herein are compositions comprising RLIP76, fragments, or modified versions thereof. The provided compositions are suitable for formulation and administration in vitro or in vivo. Optionally, the compositions comprise RLIP76 and a pharmaceutically acceptable carrier. Suitable carriers and their formulations are described in *Remington: The Science and Practice of Pharmacy*, 21st Edition, David B. Troy, ed., Lippicott Williams & Wilkins (2005), and in *Remington: The Science and Practice of Pharmacy*, 22d Edition, Loyd et al. eds., Pharmaceutical Press and Philadelphia College of Pharmacy at University of the Sciences (2012). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. Optionally, the provided compositions are formulated for oral administration. Optionally, the compositions include one or more buffers, one or more mucoadhesive polymers, one or more permeation enhancers and combinations thereof.

The compositions can be administered in a number of ways as selected by one skilled in the art and depending on whether local or systemic treatment is desired, on the target area to be treated, and other variables. The compositions are administered via any of several routes of administration, including topically, orally, parenterally, intravenously, intra-articularly, intra-vaginally, rectally, intraperitoneally, intra-muscularly, subcutaneously, intracavity, transdermally, intrahepatically, intracranially, pulmonary, nebulization/inhalation, or by installation via bronchoscopy. Optionally, the provided compositions are administered orally.

Optionally, the RLIP76 is formulated as a liposome composition or proteoliposome. Liposomes are vesicles consisting of amphipathic lipids arranged in one or more concentric bilayers. When lipids are placed in aqueous medium, the hydrophilic interaction of the lipid head groups with water results in the formation of multilamellar and unilamellar systems or vesicles which resemble biological membranes in the form of a spherical shell. Liposomes may be small (0.025-0.05 µm) to large (0.05-10 µm) multilamellar vesicles. Lipids used to prepare the liposomes can include, but are not limited to, phospholipids, sphingolipids, glycosphingolipids, saturated glycerides, steroids (e.g., cholesterol) and synthetic phospholipids. Liposomes are typically prepared by melting the lipid together in aqueous solvent with an emulsifier like POE. The agent is then added and the liposomes are generated through mixing or sonication. The agent is usually entrapped in the vesicle structure. These basic liposomes are sometimes referred to as conventional liposomes. Several other types of liposomal preparations exist, including (1) sterically stabilized liposomes, which are surface coated with an inert hydrophilic polymer, such as polyethylene glycol; (2) targeted liposomes, to which are attached targeting ligands, such as antibodies or fragments thereof, lectins, oligosaccharides or peptides (e.g., choleratoxin B (CTB) is used to target liposomes to the gastrointestinal epithelium); and (3) reactive or polymorphic liposomes, which change their phase and structure in response to a particular interaction (this group includes liposomes sensitive to ions (pH, cations), heat and light, among other stimuli). Lipids and liposomes include, but are not limited to, neutral (e.g., dioleoylphosphatidyl DOPE ethanolamine, dimyristoylphosphatidyl choline DMPC, and distearolyphosphatidyl choline) negative (e.g., dimyristoyl-phosphatidyl glycerol DMPG) and cationic (e.g., dioleoyltetramethylaminopropyl DOTAP and dioleoylphosphatidyl ethanolamine DOTMA) liposomes.

Optionally, the compositions provided herein include proteoliposomes. As used herein, a proteoliposome is generally a protein and lectin or glyco- or phospholipid combination that forms a spherical micellular-like or vesicular structure. The structures may form spontaneously or by chemical or mechanical manipulation, or combinations thereof. Proteoliposomes take advantage of the amphipathic nature of the lipid (or lectin) that causes them to form bilayers when in solution resulting in at least one of several shapes, including (a) spherical micelle with the tails inward, or (b) bimolecular sheets that are bilayers with hydrophobic tails sandwiched between hydrophilic head groups. In general, proteoliposomes may reseal themselves when torn or broken. Proteoliposomes may contain only one lectin or lipid or a variety and combination of each. Examples of phospholipids include phosphatidylcholine, sphingomyelin, phosphatidylserine, inositol phospholipids, and phosphatidylethanolamine. When used, proteoliposomes may be charged or electrically neutral and are generally used at physiological pH. They may also be structures mixed with detergent (e.g., detergent/lipid/protein, detergent/lectin/protein). Methods for preparing proteoliposomes of defined lipid-protein or lectin-protein ratios and size are well-known to one of ordinary skill in the art of molecular biology and protein/lipid biochemistry. The proteoliposomes of the disclosure can be made by any method known in the art, including methods disclosed and described in U.S. Publication No. 2005/0123594, the disclosure of which is incorporated herein in its entirety by reference. Optionally, the liposomes comprising RLIP76 or proteoliposomes are made using microfluidics, for example, by known techniques such as those described in, e.g., Pradhan et al., Anticancer Research 28:943-8 (2008) and Jahn et al., Langmuir, 23(11): 6289-93 (2007), which are incorporated by reference herein in their entireties.

Optionally, the compositions disclosed herein comprise a pharmaceutically acceptable carrier. As used herein, pharmaceutically acceptable carrier includes any and all solvents, dispersion media, coatings, antibacterial and antifungal agents, isotonic and absorption delaying agents and the like that are physiologically suitable. The use of such pharmaceutically acceptable carriers with pharmaceutical active agents is well known in the art. Except insofar as any conventional media or agent is incompatible with the active agent, its use in the compositions disclosed herein is contemplated. Supplementary active ingredients can also be incorporated into the compositions.

Optionally, the compositions comprise one or more buffers. Most commonly used buffers are salts of weak acids such as carbonates, citrates, gluconates, phosphate and tartrates. Buffers include, but are not limited to, citric acid, sodium phosphate, sodium acetate, dipotassium hydrogen phosphate, phosphoric acid, and L-methionine.

A protein can be formulated into a composition in a neutral or salt form. Pharmaceutically acceptable salts include, but are not limited to, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

As used herein, pharmaceutically-acceptable salts refer to compounds disclosed herein wherein the parent compound is modified by making acid or base salts thereof. Examples of pharmaceutically-acceptable salts include, but are not limited to, mineral or organic acid salts of basic residues such as amines; alkali or organic salts of acidic residues such as carboxylic acids; and the like. Thus, the term acid addition salt refers to the corresponding salt derivative of a parent compound that has been prepared by the addition of an acid. The pharmaceutically-acceptable salts include, but are not limited to, the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds may exist as zwitterions. All forms of the active agents, including free acid, free base, and zwitterions, are contemplated to be within the scope of the present disclosure.

RLIP76 compositions can be complexed with polyethylene glycol (PEG), metal ions, or incorporated into polymeric compounds such as polylactic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and/or rate of in vivo clearance, and are thus chosen according to the intended application.

In addition, RLIP76, or one or more active fragments or variants thereof, can be bound, for example by covalent, non-covalent, ionic, or hydrophobic bonds, with any number of different delivery vehicles, including, but not limited to, liposomes, proteoliposomes, vesicles, nanoparticles, noisosomes, carrier proteins, gold particles, chitin, polymers, organic "cages," viruses, and bacteria. In addition, preferential uptake of any of the above RLIP76 compositions by one or more specific organs, tissues, or cell types can be accomplished by the inclusion of one or more specific targeting moieties with RLIP76 or any of the delivery vehicles listed above. Such targeting moieties include, but are not limited to, antibodies, or fragments thereof, peptides, lipids, chemicals, charged particles, receptors, proteins, viral promoters, transcription factors, DNA promoters, and nucleic acids that have a particular two- or three-dimensional structure.

The disclosed compounds can be orally administered, for example, with an inert diluent or with an assimilable edible carrier, or they can be enclosed in hard or soft shell gelatin capsule, or they can be incorporated directly with the food of the diet. For oral therapeutic administration, the active compounds can be incorporated with excipients and used in the form of tablets, troches, capsules, elixirs, suspensions, syrups, wafers, and the like. Such compositions and preparations should contain at least 0.1% of active agent. The percentage of the compositions and preparations may, of course, be varied. The amount of active agents in such therapeutically useful compositions is such that a suitable dosage will be obtained.

Compositions and formulations for oral administration include, but are not limited to, powders or granules, microparticulates, nanoparticulates, suspensions or solutions in water or non-aqueous media, capsules, gel capsules, sachets, and tablets. Such compositions may also include thickeners, flavoring agents, diluents, emulsifiers, dispersing aids or binders. Optionally, the compositions formulated for oral administration include one or more buffers, one or more mucoadhesive polymers, one or more permeation enhancers and combinations thereof.

Permeation enhancers include, for example, surfactants, chelating agents, and non-chelating non-surfactants (Lee et al., Critical Reviews in Therapeutic Drug Carrier Systems, 1991). Surfactants include fatty acids and/or esters or salts thereof, bile acids and/or salts thereof. Bile acids and salts thereof include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24, 25-dihydro-fusidate, sodium glycodihydrofusidate, and sodium glycodeoxycholate (SGDC). Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Permeation enhancers also include polyoxyethylene-9-lauryl ether, polyoxyethylene-20-cetyl ether, as well as other polyoxygen containing compounds such as propylene glycol.

Tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the composition is a capsule, it may contain, in addition to materials of the above type, a liquid carrier. Various other materials may be present as coatings or to otherwise modify the physical form of the composition. For instance, tablets, pills, or capsules may be coated with shellac, sugar or both. A syrup or elixir may contain sucrose as a sweetening agent methyl and propylparabens as preservatives, a dye and flavoring, such as cherry or orange flavor. Of course, any material used in preparing any composition should be pharmaceutically pure and substantially non-toxic in the amounts employed. In addition, the active agents may be incorporated into sustained-release preparation and formulations.

Optionally, the provided compositions comprise a mucoadhesive. The mucoadhesive typically comprises a polymer with functional groups that provide adhesion to skin and stoma. The functional groups are selected from a group consisting of thiols, acids and their salts, iminothiolanes, thioalkylamidines, catechols, amino acids, dihydroxy substituted aromatic groups, and combinations thereof. The polymer is a biocompatible polymer made from natural or synthetic polymer selected from a group consisting of polyacrylates, polyakylmethacrylates, polyphenylmethacrylate, polyanhydrides, styrenic block copolymers, polyamides, polyesters, polyvinyl ethers, polyvinyl esters, sulfonated polymers, polyolefins, silicones, polyvinylpyrrolidones, polyvinylacetate and its copolymers, polyvinyl alcohol, polyurethanes, polyethers, copolymers of maleic anhydride, polysaccharides, polypeptides, gelatin, alginates, gums, starch, chitosan, pectin, and combinations thereof.

The composition may further contain other components such as liposomes, phospholipids, hydrophobic polymers, hydrophilic polymers, amphiphilic polymers, tackifiers, resins, plasticizers, hydrocolloids, inorganic and organic particulate fillers, antioxidants, and combinations thereof. Optionally, the compositions comprise hydrogenated soy phosphatidylcholine (HSPC) and propylene glycol (PG).

Optionally, the provided compositions comprise one or more mucoadhesive polymers. Polymers used in mucosal delivery may be of natural or synthetic origin. There are two broad classes of mucoadhesive polymers: hydrophilic polymer and hydrogels. Of the hydrophilic polymers, those containing carboxylic groups exhibit the best mucoadhesive properties. Mucoadhesive polymers include, but are not limited to, cellulose and its derivatives, anionic polyelectrolytes (e.g. poly (acrylic acid)), carboxymethyl cellulose (CMC), poly vinyl pyrrolidone (PVP), methyl cellulose (MC), sodium carboxy methylcellulose (SCMC), hydroxy propyl cellulose (HPC) and other cellulose derivatives. Hydrogels are three-dimensionally crosslinked polymer chains and are typically made of polymeric biomaterials including, but not limited to, polyacrylates and their crosslinked modifications (e.g., carbopol 934), and chitosan and its derivatives. Optionally, the compositions do not include carbopol 974P NF and/or Pol407, which is a copolymer of polypropylene glycol (PPG) and polyethylene glycol (PEG). Optionally, the mucoadhesive polymer is a thiolated polymer. Thiolated polymers include chitosan-iminothiolane, poly(acrylic acid)-cysteine, poly(acrylic acid)-homocysteine, chitosan-thioglycolic acid, chitosan-thioethylamidine, alginate-cysteine, poly(methacrylic acid)-cysteine and sodium carboxymethylcellulose-cysteine. Optionally, the mucoadhesive polymer is a lectin-based polymer, for example, wheat germ agglutinin.

The active agents may be administered, for example, parenterally, or intraperitoneally, although other forms of administration as described herein can be used. Solutions of the active agents as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion. Some variation in dosage will necessarily occur depending on the condition of the subject being treated. The person responsible for administration will, in any event, determine the appropriate dose for the individual subject.

The pharmaceutical forms suitable for injectable use include sterile aqueous solutions or dispersions and sterile powders for the extemporaneous preparation of sterile injectable solutions or dispersions. In all cases the form must be sterile and must be suitably fluid. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active agents in the required amount in the appropriate solvent with several of the other ingredients enumerated above, as required, followed by filtered sterilization. Generally, dispersions are prepared by incorporating the various sterilized active agents into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The disclosed compositions are optionally formulated to be administered by use of a skin patch, or transdermal delivery system. Transdermal administration can be accomplished by any of a number of systems known in the art. Examples of systems that may be adapted for use with the compositions described herein include those systems of transdermal administration described in U.S. Pat. Nos. 4,816,252; 5,122,382; 5,198,223; 5,023,084; 4,906,169; 5,145,682; 4,624,665; 4,687,481; 4,834,978; and 4,810,499, each of which is incorporated herein by reference.

The provided methods may include an adhesive matrix or drug reservoir system (e.g., for administration by a patch or pump) and may include a skin permeation enhancement agent such as ethanol, polyethylene glycol 200 dilaurate, isopropyl myristate, glycerol trioleate, linolenic acid saturated ethanol, glycerol monooleate, glycerol monolaurate, n-decyl alcohol, capric acid, and certain saturated and unsaturated fatty acids, and their esters, alcohols, monoglycerides, acetate, diethanolamides and N,Ndimethylamides (see, for examples, U.S. Pat. No. 4,906,169).

The provided compositions can be administered one or more times daily, weekly or monthly. Optionally, the composition is administered twice daily. Optionally, the composition is administered for one or more days or weeks prior to a treatment that places the subject at risk of developing mucositis. Optionally, the treatment is radiation therapy or chemotherapy. Optionally, the composition is administered for one week prior to treatment and for one or more days after treatment. Optionally, the composition is administered daily for one week prior to and for four weeks after treatment.

Optionally, the compositions comprising RLIP76, for example the RLIP76 proteoliposomes, can be used in combination with one or more additional radiation or chemotherapeutic protection agents, including, but not limited to, free radical scavengers, antioxidants, and superoxide dismutase analogs. Unprotected RLIP76 is susceptible to proteolysis, rendering administration of the bare protein challenging. To facilitate stability of the protein, RLIP76 may be administered in the form of lipid encapsulated proteoliposomes. In addition, RLIP76 protein may be administered along with one or more radiation protection agents, for example antioxidants, free radical scavengers, or superoxide dismutase analogs, to facilitate stability of the protein.

Additional free radical scavengers or antioxidants that can be used in combination with RLIP76 include, but are not limited to, butylated hydroxytoluene (BTH), N-acetylcysteine, sodium thiosulfate, glutathione ethyl ester, glutathione, D-methionine, cysteamine, cystamine, aminopropylmethylisothiourea, Ethyol, vitamin E, edaravone (3-methyl-1-phenyl-2-pyrazolin-5-one), melatonin, polynitroxyl-albumin, idebenone, nitric oxide, Carvedilol, alpha-lipoic acid, allopurinol, 2 0 octadecylascorbic acid, N-2-mercaptopropionyl glycine, superoxide dismutase (SOD), recombinant human CuZn-SOD, glutathione peroxidase, catalase, nitric oxide synthase, ascorbic acid (Vitamin C), selenium, acetylcysteine, seleginine (Deprenyl®), pycnogenol, co-enzyme Q10, beta carotene, PC 01, SC-55858, iron (III) porphyrins, mithramycin, chromomycin, daunomycin, olivomycin and WP-631, or combinations thereof.

Additional radiation protection agents that can be used in combination with RLIP76 include, but are not limited to, Fullerene DF-1, butylated hydroxyanisole (BHA), butylated hydroxytoluene (BHT), carbon nanotubes, autologous and allogeneic bone marrow derived stem cells, CD34 positive cells, protein and/or cDNA and/or mRNA for Rad51 or Rad52 and related genes, TGF beta type II receptor gene and/or products, and p53 gene and/or products, or combinations thereof.

The present disclosure encompasses methods of preventing or treating mucositis, for example resulting from radiation exposure or chemotherapy, which comprises administering to a patient or subject in need of such treatment or management a therapeutically effective amount of RLIP76 or a therapeutic combination of RLIP76 and another active agent, for example another radioprotective or an antimicrobial agent. Optionally, such a compound or dosage unit comprising RLIP76 is referred to as an active agent. Use of the disclosed compositions in the manufacture of a medicament for treating or managing a disease or disorder is also contemplated. The present disclosure also encompasses compositions comprising a biologically or therapeutically effective amount of one or more cargo molecules for use in the preparation of a medicament for use in treatment or management of mucosal disruption.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions.

As used herein, and unless otherwise indicated, the terms treat, treating, and treatment contemplate an action that occurs while a patient is suffering from a disease or disorder, that reduces the severity or delays the onset of one or more symptoms or effects of the disease or disorder, or a related disease or disorder. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, and unless otherwise indicated, the terms manage, managing, and management encompass preventing, delaying, or reducing the severity of a recurrence of a disease or disorder in a patient who has already suffered from the disease or disorder. The terms encompass modulating the threshold, development, and/or duration of the disease or disorder, or changing the way that a patient responds to the disease or disorder.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

As used herein, and unless otherwise specified, a therapeutically effective amount of a compound is an amount sufficient to provide any therapeutic benefit in the treatment or management of a disease or disorder (e.g., mucositis), or to delay or minimize one or more symptoms associated with a disease or disorder. A therapeutically effective amount of a compound means an amount of the compound, alone or in combination with one or more other therapies and/or therapeutic agents, which provides any therapeutic benefit in the treatment or management of a disease or disorder, or related diseases or disorders. The term therapeutically effective amount can encompass an amount that cures a disease or disorder, improves or reduces a disease or disorder, reduces or avoids symptoms or causes of a disease or disorder, improves overall therapy, or enhances the therapeutic efficacy of another therapeutic agent.

Toxicity and therapeutic efficacy of the described compounds and compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, expressed as the ratio LD50/ED50. Compounds that exhibit large therapeutic indices are preferred. Compounds that exhibit toxic side effects may be used in certain embodiments; however, care should usually be taken to design delivery systems that target such compounds preferentially to the site of affected tissue, in order to minimize potential damage to uninfected cells and, thereby, reduce side effects.

Data obtained from cell culture assays and animal studies can be used in formulating a range of dosages for use in humans. In certain aspects of the present disclosure, the dosages of such compounds lie within a range of circulating concentrations that include the ED50 with little or no toxicity. The dosage may vary within this range depending on the dosage form employed and the route of administration utilized. For any compound used in the disclosed methods, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Plasma levels may be measured, for example, by high performance liquid chromatography.

When therapeutic treatment is contemplated, the appropriate dosage may also be determined using animal studies to determine the maximal tolerable dose, or MTD, of a bioactive agent per kilogram weight of the test subject. In general, at least one animal species tested is mammalian. Those skilled in the art regularly extrapolate doses for efficacy and avoiding toxicity to other species, including human. Before human studies of efficacy are undertaken, Phase I clinical studies help establish safe doses. Additionally, the bioactive agent may be complexed with a variety of established compounds or structures that, for instance, enhance the stability of the bioactive agent, or otherwise enhance its pharmacological properties (e.g., increase in vivo half-life, reduce toxicity, etc.).

The provided compositions can contain from 0.1 microgram/kg body weight to 1000 mg/kg body weight of the RLIP76, or a fragment or variant thereof. Optionally, the effective dose of the composition or dosage unit can be in the range of about 14 mg/kg to about 0.01 mg/kg, about 14 mg/kg to about 0.025 mg/kg, about 14 mg/kg to about 0.05 mg/kg, about 14 mg/kg to about 0.1 mg/kg, about 14 mg/kg to about 0.25 mg/kg, about 14 mg/kg to about 0.5 mg/kg, about 14 mg/kg to about 1 mg/kg, about 14 mg/kg to about 2.5 mg/kg, about 14 mg/kg to about 5 mg/kg, about 5 mg/kg to about 0.01 mg/kg, about 2.5 mg/kg to about 0.01 mg/kg, about 1 mg/kg to about 0.01 mg/kg, about 0.5 mg/kg to about 0.01 mg/kg, about 0.25 mg/kg to about 0.01 mg/kg, about 0.1 mg/kg to about 0.01 mg/kg, about 0.05 mg/kg to about 0.01 mg/kg, about 0.025 mg/kg to about 0.01 mg/kg, about 5 mg/kg to about 0.025 mg/kg, about 2.5 mg/kg to about 0.05 mg/kg, about 1 mg/kg to about 0.1 mg/kg, about 0.5 mg/kg to about 0.25 mg/kg, or about 3 mg/kg to about 0.1 mg/kg, or so. Thus, in particular embodiments, the effective dose of the composition or dosage unit is about 0.01 mg/kg, about 0.025 mg/kg, about 0.05 mg/kg, about 0.075 mg/kg, about 0.1 mg/kg, about 0.25 mg/kg, about 0.5 mg/kg, about 0.75 mg/kg, about 1 mg/kg, about 2.5 mg/kg, about 3 mg/kg, about 5 mg/kg, about 7.5 mg/kg, about 10 mg/kg, about 11 mg/kg, about 12 mg/kg, about 13 mg/kg, about 14 mg/kg, or so.

A subject may be a cancer patient. Examples include but are not limited to cancer of the breast colon, ovaries, central nervous system, liver, bladder, pancreas, cervix, melanoma and leukemia. In some embodiments, the subject is previously or subsequently exposed to radiation treatment or to a chemotherapeutic agent or a combination thereof.

Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood', Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland'Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

A typical kit comprises one or more dosage units of a composition comprising RLIP76, or a pharmaceutically acceptable salt, prodrug, solvate, hydrate, or stereoisomer thereof. Active fragments and variants of RLIP76 can also be used. Optionally, one or more dosage units of another agent, for example a radioprotective agent, may be included in the kits. Kits can further comprise devices that are used to administer the active ingredients. Examples of such devices include, but are not limited to, syringes, drip bags, patches, and inhalers. Optionally, the kits include instructions for use.

The disclosed kits can further comprise pharmaceutically acceptable vehicles that can be used to administer one or more disclosed compositions. For example, if a disclosed composition is provided in a solid form that is to be reconstituted for parenteral administration, the kit can comprise a sealed container of a suitable vehicle in which the disclosed composition can be dissolved to form a particulate-free sterile solution that is suitable for parenteral administration. Examples of pharmaceutically acceptable vehicles include, but are not limited to, water; aqueous vehicles such as, but not limited to, sodium chloride injection, Ringer's injection, dextrose injection, dextrose and sodium chloride injection, and lactated Ringer's injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Those of skill in the art should, in light of the present disclosure, appreciate that many changes can be made in the specific embodiments which are disclosed and still obtain a like or similar result without departing from the spirit and scope of the invention. The present application is not to be limited in scope by the specific embodiments described herein, which are intended as single illustrations of individual aspects, and functionally equivalent methods and components are within the scope of the claims. Indeed, various modifications, in addition to those shown and described herein, will become apparent to those skilled in the art from the foregoing description.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a composition is disclosed and discussed and a number of modifications that can be made to a number of molecules including the composition are discussed, each and every combination and permutation of the composition, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims below.

EXAMPLES

Example 1

RLIP76-PL has Localized Tissue Uptake

Effective drug absorption by the oral mucosa is one of the challenges for OM treatments. Based on preliminary data for topical administration of RLIP76 liposome in a mucoadhesive polymer, it is expected to be locally absorbed from the oral mucosa and not enter systemic circulation. Using the IVIS imaging system and a fluorescently labeled RLIP76-PL, a difference could be detected at early timepoints after RLIP76-PL was applied to the cheeks of mice (FIG. 1). The data indicate that there is immediate absorption of the labeled drug. The lack of difference after 20 minutes may be explained by the liquidity of the drug formulation as it is likely that the liquid formulation did not adhere to the cheek for an extended time, and was swallowed. This preliminary study demonstrated that a more viscous formulation will be required for use in the mouse model.

Example 2

Formulation Study of RLIP76-PL for Increased Efficacy as a Local Oral Topical

Different formulations were evaluated to make a liposomal suspension for parenteral injection and systemic delivery into a formulation suitable for local delivery to healthy mucosa tissue of the oral cavity.

Fourteen formulation candidates for the prevention of radiation-induced oral mucositis were identified through literature searches and analyses. However, after careful consideration, five (5) of these initial candidate formulations were discounted due to predicted incompatibilities with the RLIP76 protein or RLIP76-proteoliposomal (RLIP76-PL) formulation. Nine formulations were manufactured and placed on a four-week stability study, where physiochemical tests were performed weekly. At the end of the stability study, five (5) additional candidate formulations were discounted on the basis of physiochemical testing results. The remaining four (4) candidate formulations were evaluated in an in vitro permeation study to further down select to two (2) candidate formulations for use.

The key modifications to the RLIP76-PL formulation to develop a set of candidate local oral topical formulations are the addition of mucoadhesives and/or permeation enhancers. Those selected for characterization included:

Carboxymethyl cellulose (CMC) significantly increases the viscosity of the proteoliposome suspension and imparts mucoadhesive properties via hydrogen bonding with the mucosal surface.

Poloxamer 407 (Pol407) is a thermoresponsive co-polymer of polypropylene glycol and polyethylene glycol that, at the right concentrations, changes in viscosity in response to changes in temperature.

Carbopol 974P NF (CP974) is a high molecular weight, highly cross-linked polymer of acrylic acid. When used in oral topical formulations, it creates mucoadhesion with the mucosa by hydrogen bonding, increasing the retention time of the formulation in the oral cavity.

Poly(acrylic acid) (PAA), a highly cross-linked polymer of acrylic acid, also undergoes mucoadhesion by hydrogen bonding with the mucosal surface and was chosen as an alternative to CP974 because it has a higher molecular weight. Like CP974, PAA has mucoadhesive properties that can extend the retention time of the formulation in the oral cavity.

Hydrogenated soy phosphatidylcholine (HSPC) and propylene glycol (PG) together form a deformable liposome (ethosomes) capable of fluidizing and penetrating the oral mucosal epithelium.

Sodium glycodeoxycholate (SGDC) is a bile salt with surfactant like properties. It has been shown that SGDC enhances epithelial permeation by slightly causing the cells to swell and become leakier.

Two of the candidates listed above (Pol407 and CP974) were found to be incompatible with RLIP76-PL and were not carried forward. When Pol407 was dissolved into a solution of RLIP76 protein in parenteral buffer, the Pol407 and protein precipitated. Solutions of CP974 could be made in water, but not in parenteral buffer, indicating an incompatibility with one or more of the RLIP76-PL buffer components. The primary incompatibility was determined to be with sodium chloride, a necessary part of the RLIP76-PL buffer for the stability and solubility of RLIP76 protein.

The two remaining mucoadhesives (CMC and PAA) and two permeation enhancers (PG and SGDC) were found to be compatible with RLIP76-PL and carried forward for evaluation separately and in combination to create nine distinct formulations. The compatibility was then assessed for each mucoadhesive and permeation enhancer in parenteral buffer, with RLIP76 protein in parenteral buffer, and with RLIP76-PL in parenteral buffer.

Two formulations of RLIP76-PL containing CMC (2% and 3.5%) were developed and monitored for stability over 4 weeks. Concentrations greater than 4% were too viscous to advance (Designations: RLIP76-PL/CMC 2% and RLIP76-PL/CMC 3.5%). A RLIP76-PL containing 5% PAA (w/v) was prepared and monitored for stability over 4 weeks (Designation: RLIP76-PL/PAA).

There were three permeation enhancer candidates. A formulation of RLIP76-PL using a HSPC liposome with 10% PG was produced and characterized for stability (Designation: RLIP76-PL(HSPC)/PG). A second 10% PG containing formulation was produced, using the standard lipid composition [HSPC, cholesterol, and 1,2-dioctadecanoyl-sn-glycerol-3' phospho-(1'-rac-glycerol) (DSPG)] (Designation: RLIP76-PL/PG). A RLIP76-PL formulation containing 5% SGDC was developed and monitored for stability over 4 weeks (Designation: RLIP76-PL/SGDC).

There were three combination candidates. RLIP76-PL using a HSPC liposome with 10% PG and 2% CMC was prepared and placed on stability for 4 weeks (Designation: RLIP76-PL(HSPC)/PG+CMC). RLIP76-PL formulation composed of HSPC, CH, and DSPG with 10% PG and 2% CMC was prepared and placed on stability for 4 weeks (Designation: RLIP76-PL/PG+CMC). RLIP76-PL formulation containing 5% SGDC and 2% CMC was placed on stability for 4 weeks (Designation: RLIP76-PL/SGDC+CMC).

Each formulation developed was characterized for stability and key criteria, described in Table 2, over a period of four weeks, at one-week intervals, to develop a usable timeframe as a liquid formulation.

TABLE 2

Summary of oral mucositis RLIP76-PL formulation selection criteria.

| Parameter | Test Method | Criteria | Relevance |
| --- | --- | --- | --- |
| Appearance | Visual/Microscope | Turbid solution, Free of particulates | Particulates indicate the suspension is unstable and aggregating |
| Suspension pH | USP <791> | 7.0-7.6 | Acidic/basic solutions may precipitate the protein, may cause discomfort to patient |
| Bioburden | SOP# 13,006, USP <61>, USP <62>, USP <1111> | NMT 20 | Bioburden may cause an infection in patients |
| Protein Concentration | SOP# 13,000 | 0.9-1.1 mg/ml | Ensures correct dose of RLIP76 protein is being administered |
| Protein Entrapment | SOP# 13,009 | >80% | Terapio studies demonstrate that RLIP76 protein must be entrapped to be effective |
| Particle Size Distribution | SOP# 13,012 | >1,000 nm | Changes in particle size distribution indicate a suspension instability |
| Zeta Potential | SOP# 13,026 | ±10% of starting material | Change in surface charge indicate the protein/lipid structure may be instable |

Figure 2:
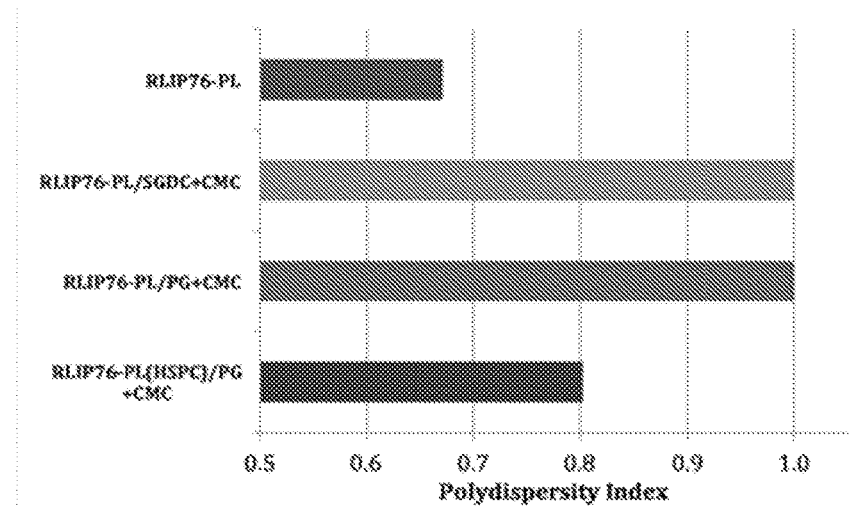
FIG. 2 is a graph showing the polydispersity index of permeation enhancer and mucoadhesive combination formulations. The polydispersity index (PDI) is an indication of the variability of particle size distribution. As the PDI reaches a value of 1.0, the particulate distribution is highly variable with multiple size populations. Combination formulations of PG and CMC, and SGDC and CMC resulted in highly polydispersed particulate distributions that were greater than that of the RLIP76-PL parenteral formulation.

Beside the particle size radius noted in Table 2, another important metric for particle size distribution is the polydispersity index (PDI). The PDI is reported as a number between 0 and 1.0, where values closer to zero represent a homogenous and "tight" distribution. As shown in FIG. 2, the RLIP76-PL formulation for a radiation MCM has a PDI of ~0.6, where the combination candidates for oral mucositis have a PDI>0.8. In fact, the RLIP76-PL/PG+CMC and RLIP76-PL/SGDC+CMC formulations had a PDI of 1.0 and remained at 1.0 for the four-week stability study. The strong disparity of the particle size distributions of these combination candidates from the baseline radiation medical counter measure (MCM) formulation makes their success in an in vivo efficacy study unlikely and therefore were not selected for further evaluation.

Based on physiochemical analysis, four candidates were selected for further evaluation via an in vitro permeability test:
    RLIP76-PL containing 2% CMC (w/v)
    RLIP76-PL containing 5% PAA (w/v)
    RLIP76-PL using a HSPC liposome with 10% PG (v/v)
    RLIP76-PL formulation containing 5% SGDC (w/v)

Figure 5:
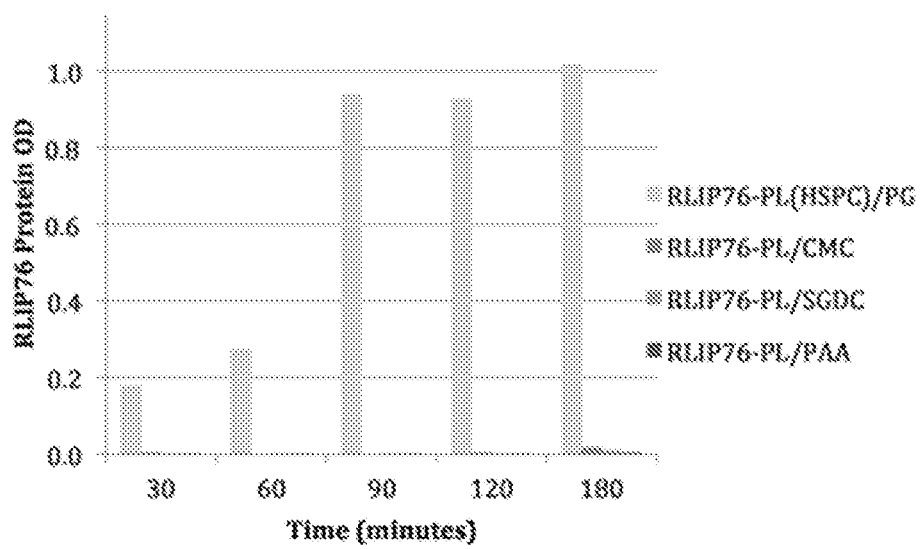
FIG. 5 is a graph showing detection of RLIP76 protein in receiver compartment of Franz diffusion cell over time. Candidate formulations were evaluated for their ability to permeate porcine buccal tissue using a Franz diffusion cell. The RLIP76-PL (HSPC)/PG formulation was strongly detected in the receiver compartment over the sampling period, compared to the other formulations. RLIP76-PL/CMC, RLIP76-PL/SGDC, and RLIP76-PL/PAA were only slightly detectable in the receiver compartment beginning at 180 minutes.
Figure 6:
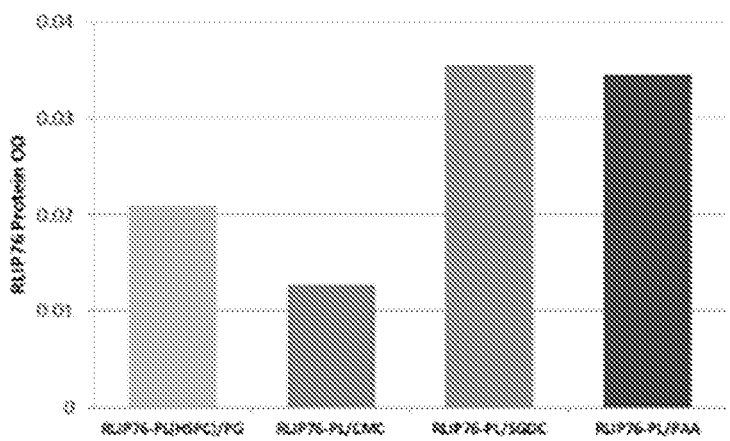
FIG. 6 is a graph showing detection of RLIP76 protein in buccal tissue. The accumulation of candidate formulations in porcine buccal tissue was determined. All formulations were detectable in buccal tissue with RLIP76-PL/SGDC and RLIP76-PL/PAA having the highest detection, followed by RLIP76-PL(HSPC)/PG and RLIP76-PL/CMC.

To characterize the permeability of the candidate oral mucositis formulations, an in vitro porcine buccal tissue permeability test was performed using a Franz diffusion cell. The four RLIP76-PL formulations were incubated on the mucosa side of the tissue for 3 hours, and samples were collected from the receiver compartment at regular intervals (30, 60, 90, 120, and 180 min). At the end of the incubation period, tissues were collected, rinsed three times, and homogenized. Tissue homogenates and solutions from the receiver compartment were analyzed for RLIP76 protein by ELISA. The control was incubated with a solution of atenolol and testosterone (atenolol, but not testosterone, will permeate an intact cheek tissue). FIG. 5 shows detection of RLIP76 protein in the receiver compartment over time. RLIP76-PL(HSPC)/PG was the only formulation that permeated the buccal tissue and was detectable in the receiver compartment. Shown in FIG. 6 is RLIP76 protein detected in the buccal tissue following three hours of incubation.

As mentioned above, an oral mucositis formulation can be a mouthwash or liquid spray and needs to be well tolerated by patients. To do so, the formulation viscosity and texture needs to be low and smooth. CMC significantly increases the viscosity of the solution, and concentrations greater than 4% (w/v) formed a semi-solid gel. The mucoadhesive candidate containing 2% (w/v) CMC had a viscous, but usable consistency, where the formulation containing 3.5% (w/v) CMC was difficult to pipet.

Figure 3:
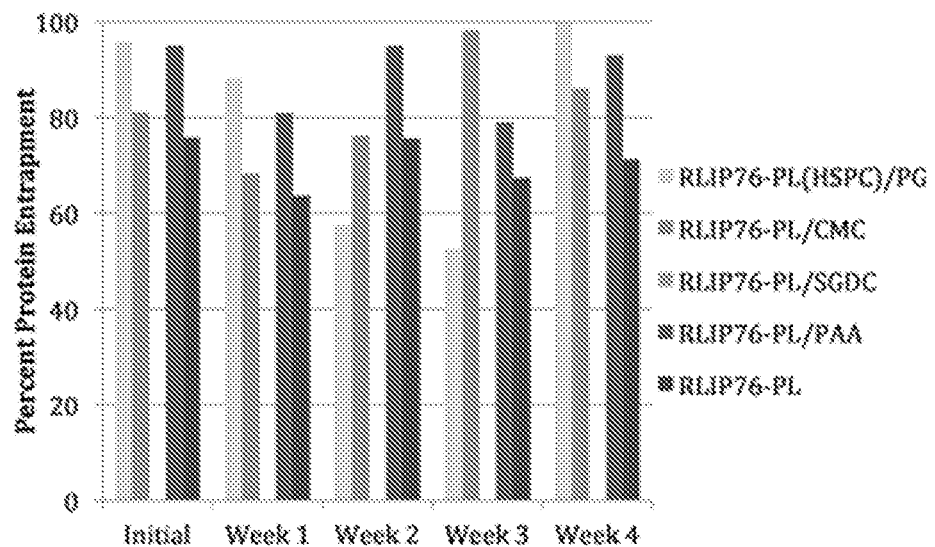
FIG. 3 is a graph showing the protein entrapment of candidate formulations during four (4) weeks of stability. Protein entrapment represents the percent of the RLIP76 protein that is contained within the liposome. Candidate formulations were within specification, with RLIP76-PL (HSPC)/PG being an exception. The percent protein entrapment decreased from the initial measurement through week 3. The RLIP76-PL/SGDC protein entrapment data are absent due to an incompatibility between SGDC and the protein detection assay.
Figure 4:
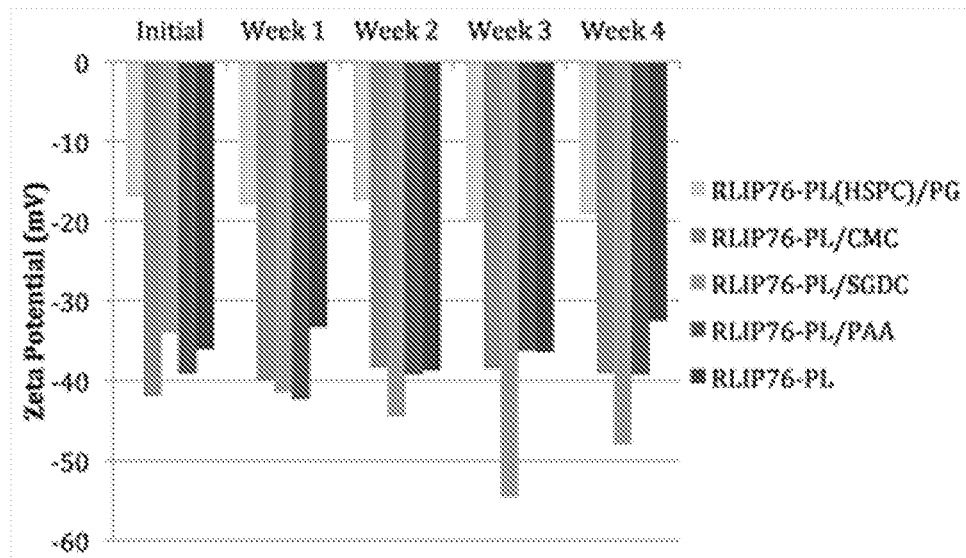
FIG. 4 is a graph showing zeta potential of candidate formulations during four (4) weeks of stability. Zeta potential is a measure of the particulate's surface charge. Changes in zeta potential from week to week indicate instability in the protein-in-lipid distribution. All formulations were found to be within specification and stable over time. An exception being RLIP76-PL/SGDC, where the zeta potential decreased from −35 mV to −55 mV by week 3.

The four remaining candidate formulations represent each of the compatible mucoadhesive and permeation enhancer chemicals including RLIP76-PL/CMC, RLIP76-PL/PAA, RLIP76-PL(HSPC)/PG, and RLIP76-PL/SGDC. All formulations had reasonable physiochemical stability over the four weeks test. Their visual appearances were opalescent with a smooth texture and were grey to off-white in color. No RLIP76 protein precipitation was evident while observing under the microscope. Solution characteristics of pH, conductivity and concentration were within specification and consistent from week to week. FIG. 3 shows the RLIP76 protein entrapment data of the candidate formulations over time (SGDC was found to be incompatible with our protein detection assay, results not shown). The formulation candidate RLIP76-PL(HSPC)/PG demonstrated a steady decrease in entrapment from the initial to week 3 measurement. The observed decrease in protein entrapment was attributed to the "leakiness" of the fluidize membrane in the HSPC/PG system, and verified the desired intent for a faster releasing liposome. The sharp increase in protein entrapment at week 4 may have been an artifact of the protein entrapment assay, or aggregation of the now released protein. The zeta potential, another indication of the particulate stability in solution, indicated that the formulations were stable (FIG. 4) with the exception of RLIP76-PL/SGDC. This change indicates that the protein distribution within the liposome or liposome agglomeration is occurring.

All formulations tested in vitro had a positive RLIP76 signal in the tissue homogenate. RLIP76-PL/CMC had the lowest average signal and was therefore not selected, while RLIP76-PL/SGDC and RLIP76-PL/PAA had equivalent absorbed levels of RLIP76 protein. Due to challenges of characterizing the SGDC formulation (protein entrapment and zeta potential), it was not selected. Based on physiochemical characterization and the absorption/permeation data obtained from the in vitro testing, RLIP76-PL formulations composed of (1) HSPC and 10% PG and (2) 5% PAA were selected for in vivo efficacy testing.

Example 3

Characterization of Effects of Selected Formulations of RLIP76-PL in a Hamster Model To demonstrate the efficacy in vivo of at least one candidate formulation of RLIP76-PL, two formulations were tested in a radiation-induced oral mucositis hamster model. The protocol used hamsters exposed to an acute radiation dose of 40 Gy directed to their left buccal cheek pouch to induce oral mucositis. There were two different dosing regimens of RLIP76-PL being evaluated to determine if starting prior to or at the time of irradiation has an impact on outcome. Hamsters had their interior cheek pouches "coated" with the RLIP76-PL formulation twice-daily beginning either 7 days prior to irradiation, or on the day of irradiation (Study Day 0) and twice-daily treatments continue until study termination. Clinical observations and mucositis scoring were conducted on each hamster until Day 28 of the study. Efficacy was determined based on statistical differences between treated groups and controls, where the following variables are analyzed: difference in the number of days hamsters in each group had severe mucositis, rank sum differences in daily mucositis scores, and differences in overall changes in body weight.

The hamster model is a high barrier screen as it uses an acute dose of a high radiation level directly to the cheek pouch. Clinical scoring definitions were utilized to describe the development of OM over the course of 28 days. Photographs of the affected cheeks are scored in a blinded fashion prior to statistical analysis. Two RLIP76-PL formulations were tested at two different dosing regimens (Table 3) administered pre-exposure in hamsters (n=8).

TABLE 3

Study Design

| Group # | Treatment | Dosing Route/Schedule |
|---|---|---|
| 1 | Empty Liposomes (control) | Topical-B.I.D. Day 0 to 28 |
| 2 | RLIP76-PL (F1) | Topical-B.I.D. Day 0 to 28 |
| 3 | RLIP76-PL (F1) | Topical-B.I.D. Day-7 to 28 |
| 4 | RLIP76-PL (F2) | Topical-B.I.D. Day 0 to 28 |
| 5 | RLIP76-PL (F2) | Topical-B.I.D. Day-7 to 28 |

Endpoints were based on the determination of statistical differences between treated groups and controls, when the following variables are analyzed: a) difference in the number of days hamsters in each group had severe (score≥3) mucositis; b) rank sum differences in daily mucositis scores; and c) differences in overall changes in body weight.

The grade of mucositis was scored, beginning on Day 6 and every second day thereafter (Days 8, 10, 12, 14, 16, 18, 20, 22, 24, 26, and 28). Mucositis was scored visually by comparison to a validated photographic scale, ranging from 0 for normal, to 5 for severe ulceration in virtually the entire pouch (descriptions as used in clinical scoring). The blinded photographs were used for the statistical analysis (tests employed were the Mann-Whitney Rank Sum test and chi-square analysis with a critical value of 0.05).

All predefined endpoints were successfully met, by at least one formulation tested. The results are summarized, by endpoint criterion:

i) Duration of Mucositis: Measured as the total number of days in which an animal exhibited an elevated score (≥3) and expressed as a percentage of the total number of days scored for each group. Statistical significance was calculated using chi-squared analysis. For the vehicle control group (liposomal preparations without RLIP76), this was percentage of days with a mucositis score of ≥3 and was 62.5%, over the course of the 35 day study. This percentage of days was significantly lower with both formulations in groups where treatment began seven days before irradiation (F1—51%, F2—52%). Neither formulation was effective when administration began at the time of radiation.

ii) Mucositis Scores: performed as an analysis of the severity of mucositis compared to the control group on each day (Days 6-28). Both F1 and F2 formulations demonstrated decreased mucositis scores compared to the control group when begun seven days prior to exposure, with F1 showing reduction on Days 10, 14, and 28 while F2 had a two consecutive day reduction on Days 12 and 14. The F1 formulation begun at the time of radiation had one significant two-day reduction late in the study (days 26-28).

iii) Body Weight: There were no significant differences in mean percent weight change between the controls and the treated groups As shown in Table 4, treatment with both formulations, on both schedules, lead to numerous days of reduction in the percentage of animals with ulceration, particularly towards the end of the study. There was also a marked decrease in percent ulceration on Day 14 for treatment groups including RLIP76-PL F1 (Day −7-28), RLIP76-PL F2 (Day 0-28), and RLIP76-PL F2 (Day −7-28).

The goal was to decrease overall mucositis severity scores by 15% or to show a decrease in the rank sum differences in daily mucositis scores. The predefined criteria for "overall severity" was defined as a mucositis score≥3; when data were evaluated in accordance with that criteria, then treated hamsters in several groups achieved success for reduction by 15% (summarized in Table 4). Both formulations also reached the success criteria for reducing rank sum differences in daily mucositis scores. In total, for F1, reduction was achieved on 5 days and for F2 on 2 days. Although both formulations met success criteria for decreasing mucositis severity, F1 had more days with higher percentage of reduction.

TABLE 4

Summary of timepoints at which mucositis severity reduction meets the milestone definition. (Numbers in bold font indicate timepoints exceeding success criteria.)

| Group | Percent Reduction by Day (Compared to Controls on Same Day) | | | |
|---|---|---|---|---|
| | 14 | 24 | 26 | 28 |
| RLIP76-PL F1 (Day 0-28) | 0% | 25% | 38% | 38% |
| RLIP76-PL F1 (Day-7-28) | 62% | 12% | 25% | 38% |
| RLIP76-PL F2 (Day 0-28) | 25% | 12% | 38% | 0% |
| RLIP76-PL F2 (Day-7-28) | 50% | 12% | 38% | 25% |

Example 4

Determine Systemic Distribution of the Oral Formulation of RLIP76-PL

This study evaluated whether an oral topical formulation of RLIP76-PL administered to the cheek pouch had detectable systemic distribution through the blood. In this study, Golden Syrian hamster were administered His-RLIP76-PL (proteoliposomes prepared using His-tagged RLIP76 protein) to the cheek pouch of the animals (group 2). The cheek tissue and several additional organs as well as blood were harvested at different time points up to 8 h post-treatment. Empty liposomes (containing no His-RLIP76 protein) were administered to a control group (group 1) and the same organs and blood samples were taken as in group 2 were harvested at the same time points. The concentration of His-RLIP76 protein was determined in serum samples from animals sacrificed at the various time points after applying the His-RLIP76-PL formulation. The results demonstrate detectable levels of RLIP76 protein in treated cheek tissue but undetectable RLIP76 in the serum at all time points.

TABLE 5

Biomodels study TPO-04 design. His-RLIP76 protein concentration in the His-RLIP76-PL was 0.5 mg/mL.

| Group Number | Number of Animals | Treatment | Dosing Route/ Schedule | Dosing Volume | Sacrifice Schedule (Day 0-Post Dosing) |
|---|---|---|---|---|---|
| 1 | 18 males | Empty Liposomes (control) | Topical- Once on Day 0 | 0.2 mL per dose | n = 3/time point: 0, 10, 30 min; 2, 4, 8 hrs |
| 2 | 36 males | His-RLIP76-PL | Topical- Once on Day 0 | 0.2 mL per dose | n = 6/time point: 0, 10, 30 min; 2, 4, 8 hrs |

Provided herein is RLIP76 protein tagged with a N-terminal poly-histidine peptide (His-RLIP76). This tagged RLIP76 was the same product used for in vitro cheek tissue detection in Example 2. The His-RLIP76 protein was encapsulated into a liposome and the drug was applied to the left cheek pouch (100 μg/pouch) of Syrian Gold hamsters. His-tagged RLIP76 protein from the applied drug was detected specifically by capturing His-RLIP76 protein using nickel (Ni)-coated ELISA plates which have an affinity to bind histidine-tagged proteins. Upon euthanasia, blood was collected for preparation of serum and snap frozen in liquid nitrogen.

Serum samples were used without further processing before dilutions for the assays. His-RLIP76 protein concentration in serum was determined using an ELISA capturing His-RLIP76 protein on Ni-coated ELISA plates. Detection was performed using a specific mouse anti-RLIP76 protein antibody and using anti-mouse IgG-biotin and Streptavidin-HRP in combination with the colorimetric reagent Tetramethylbenzidine (TMB). The results were analyzed using the ELISA reader's software.

A standard curve ranging from 400 ng/mL to 6.25 ng/mL in PBS/1% BSA was prepared using the His-RLIP76 standard stock. PBS/1% BSA served as blank. The serum samples were assayed at a 1:4 or 1:8 dilution to minimize matrix effects. All sample dilutions were prepared in PBS/1% BSA.

Figure 7:
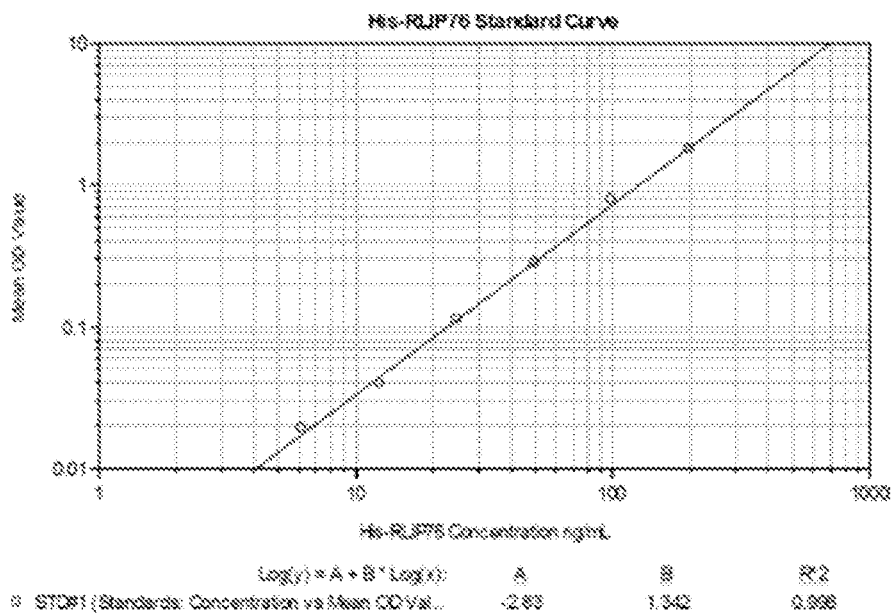
FIG. 7 is a graph showing a typical His-RLIP76 protein standard curve.

Standard and samples were added to the Ni-coated plate and incubated for 2 hours at room temperature (RT). The plate was then washed 3 times with 300 μL ELISA wash buffer/well and blotted to remove excess buffer. Anti-RLIP76 antibody at a 1:2000 dilution in PBS/1% BSA (100 μL/well anti-RALBP1 MO2) was added to the wells and the plate incubated for 2 hr at RT. The plate was again washed 3 times with 300 μL ELISA wash buffer/well and blotted to remove excess liquid. A 1:20,0000 dilution of the goat anti-Mouse IgG (H+L)-biotin antibody dilution was prepared in PBS/1% BSA and 100 μL was added to each well. The plate was incubated for 1 h at 37° C. The plate was washed 3 times with 300 μL ELISA wash buffer/well and blotted to remove excess liquid. The streptavidin-HRP conjugate was prepared at a 1:10,000 dilution in PBS/1% BSA. One hundred microliter of conjugate was added to each well and the plate incubated for 1 h at 37° C. The plate was then carefully washed 3 times with 300 μL ELISA wash buffer/well and blotted to remove excess liquid. TMB colorimetric reagent was added to the plate (100 μL/well) and incubated at room temperature for approx. 5 min before 100 μL/well of 0.2 M H2SO4 stopped the reaction. Absorption in the plate was read at 450 nm in a microplate ELISA reader. The SoftMax Pro V4.8 reader software was used to calculate sample concentrations using a log-log regression for the standard curve (FIG. 7).

Figure 8:
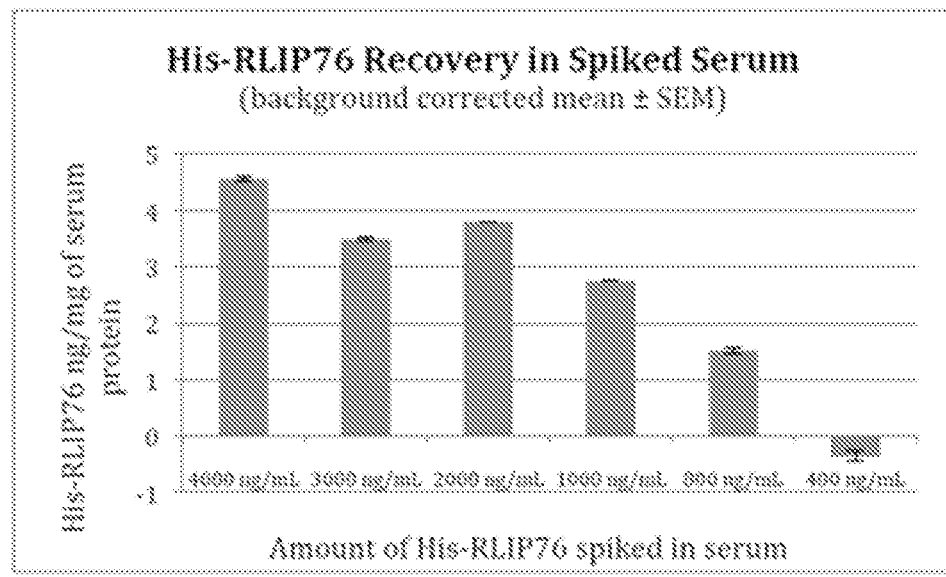
FIG. 8 is a graph showing the detection limit of His-RLIP76 in hamster serum using Ni coated plate ELISA.

The concentration of His-RLIP76 protein was determined in serum (previously frozen and stored at −80° C.) using an ELISA specific for histidine-tagged protein. The limit of detection of His-RLIP76 in the ELISA was determined using pooled serum from the empty liposome treatment group at 0 time point into which varying amounts of His-RLIP76 had been spiked ranging from 400 ng to 4000 ng of RLIP76, per mL of serum. Un-spiked serum was used as background. To maximize recovery each pool was analyzed in the ELISA at a 1:8 dilution to minimize interference from serum proteins. FIG. 8 shows that the lower limit of detection for this assay is 800 ng of His-RLIP76 per mL of serum at a serum dilution of 1:8. This would correspond to a serum concentration of approximately 10 nM.

Figure 9:
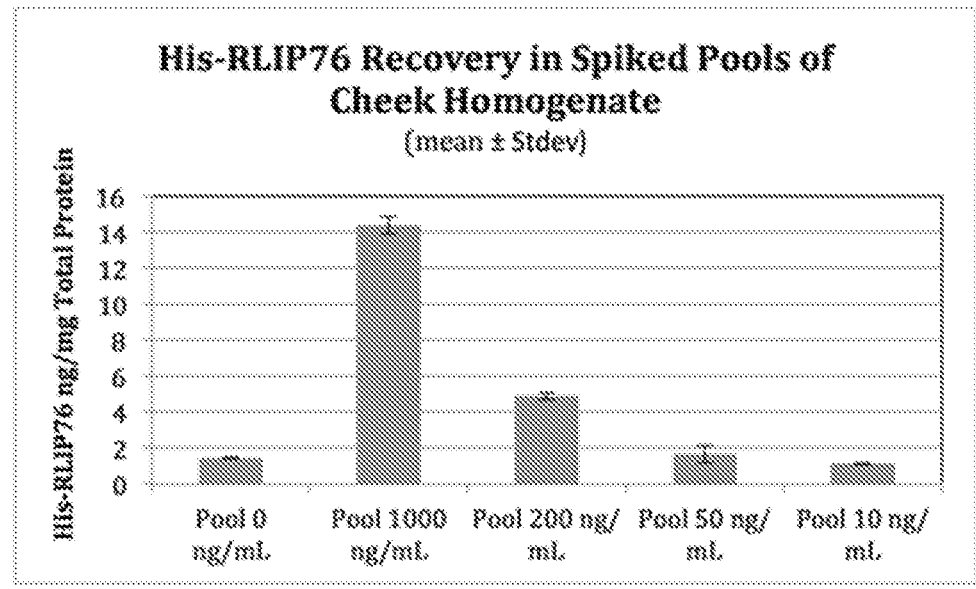
FIG. 9 is a graph showing the detection limit of His-RLIP76 in hamster cheek extracts using Ni coated plate ELISA Determination of biodistribution time course of RLIP76-PL in hamster serum and cheek.

Similarly, the limit of detection in hamster cheek tissue was determined from the empty liposome treatment group into which His-RLIP76 has been spiked directly into cheek tissues prior to sample processing. Cheek samples were spiked with 1000 ng/mL, 200 ng/mL, 50 ng/mL and 10 ng/mL of His-RLIP76 standard and the final extract was diluted 1:2 prior to analysis. An un-spiked sample was used as a control. FIG. 9 shows a dose depended response to the positive control spiked samples and detection of 200 ng of His-RLIP76/mL at a dilution of 1:2 corresponding to a lower limit of detection of 2.5 nM RLIP76 for this assay.

Due to the inherent variability of an ELISA assay across plates when trying to compare different sample types, samples selected from each cohort were directly compared levels of His-RLIP76/mL in the serum and cheeks at each of the study time points. Samples from the empty liposome group were used as controls. This analysis was then duplicated to ensure the accuracy of the results.

Figure 10:
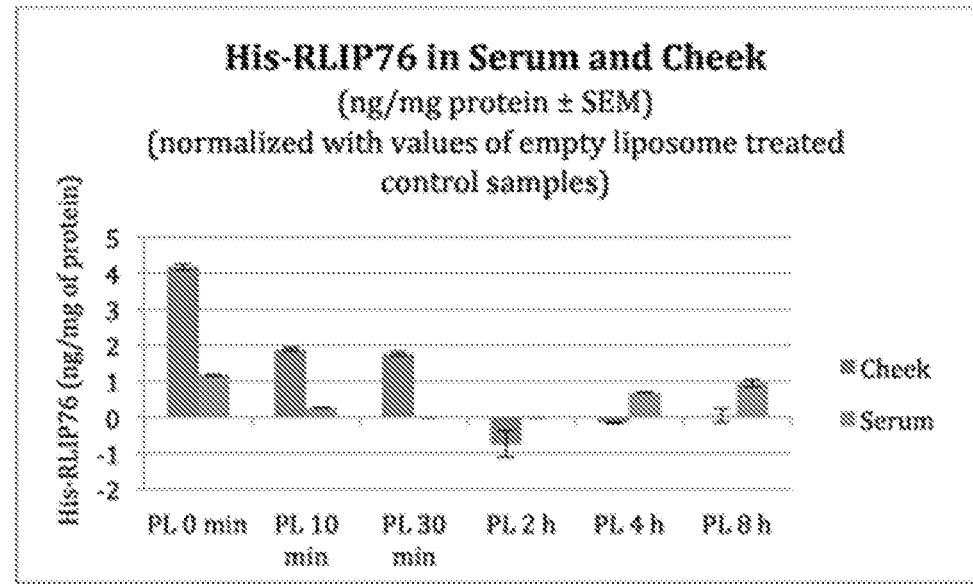
FIG. 10 is a graph showing the comparison of His-RLIP76 level in serum and cheek samples.

The results presented in FIG. 10 demonstrate detectable RLIP76 protein in the cheeks of treated animals with a time dependent loss of protein. This data verifies the ability of the assay to detect His-RLIP76 in cheeks of treated animals, that the animals were properly dosed, and supports the in vitro cheek tissue findings. Notably, serum samples at all time points did not have detectable RLIP76 protein.

Sample spiking studies in both cheek and serum demonstrated the assay's ability to detect His-RLIP76. The direct analysis of check tissue demonstrated a clear signal to verify the animals were properly dosed, and check tissue uptake occurred as expected. Finally, no His-RLIP76 was detected in the serum of the His-RLIP76-PL treated groups at any time point above the assay limited of detection of 800 ng/mL or 0.8 µg/mL. An liposomal formulation of RLIP76 protein was developed for the treatment of acute radiation syndrome. Data from several radiation countermeasure efficacy studies conducted in mice demonstrated the effective dose to be 100 µg per administration. Based on these data, a 100 µg per administration dose was further tested and an efficacious response was demonstrated. Given that a mouse has approximately 1.5 mL of blood, the effective concentration in mice calculates to be 1.3 µM Therefore, the ELISA detection limit of 10 nM is more than adequate to detect meaningful concentrations of RLIP76 protein in the blood samples. Taken together these results demonstrate that no systemic distribution of His-RLIP76 protein was detected at the tested efficacious dose level of His-RLIP76-PL.

What is claimed is:

1. A method for preventing exacerbation of or treating mucositis, comprising administering to a subject having mucositis a composition comprising RLIP76, wherein administration prevents exacerbation of or treats mucositis in the subject.

2. The method of claim 1, wherein the composition is formulated for oral administration.

3. The method of claim 1, wherein the composition further comprises one or more buffers.

4. The method of claim 3, wherein the buffer is selected from the group consisting of citric acid, sodium phosphate, phosphoric acid and L-methionine.

5. The method of claim 1, wherein the composition comprises a mucoadhesive polymer.

6. The method of claim 5, wherein the mucoadhesive polymer is a hydrophilic polymer.

7. The method of claim 1, wherein the composition comprises hydrogenated soy phosphatidylcholine, polyacrylic acid, propylene glycol, carboxymethyl cellulose, sodium glycodeoxycholate or a combination thereof.

8. The method of claim 1, wherein the composition comprises hydrogentated soy phosphatidylcholine and propylene glycol.

9. The method of claim 1, wherein the composition comprises a polyacrylic acid.

10. The method of claim 1, wherein the composition comprises sodium glycodeoxycholate or carboxymethyl cellulose.

11. The method of claim 1, wherein the composition comprises a liposome.

12. The method of claim 11, wherein the liposome comprises lectins, glycolipids, phospholipids or combinations thereof.

13. The method of claim 1, wherein administration reduces the severity of one or more symptoms of mucositis.

14. The method of claim 1, wherein the mucositis is caused by radiation exposure.

15. The method of claim 1, wherein the mucositis is caused by chemical exposure.

16. The method of claim 1, wherein the mucositis is caused by exposure to a chemotherapeutic agent.

17. The method of claim 1, wherein the mucositis is gastrointestinal mucositis.

18. The method of claim 1, wherein the mucositis is oral mucositis.

19. The method of claim 1, wherein the composition is administered one or more times daily, weekly or monthly.

20. The method of claim 19, wherein the composition is administered twice daily.

21. The method of claim 1, wherein the composition comprises from 0.1microgram/kg body weight to 1000 mg/kg body weight of the RLIP76.

22. The method of claim 1, further comprising the step of administering antimicrobial therapy to the subject.

23. The method of claim 22, wherein the antimicrobial therapy is antibiotic therapy.

24. A method for preventing or treating mucositis, comprising administering to a subject having cancer a composition comprising RLIP76, wherein administration prevents or treats mucositis in the subect.

25. The method of claim 24, wherein administration of the composition occurs prior to, concurrently with, or after a treatment that places the subject at risk of developing mucositis.

26. The method of claim 25, wherein administration occurs prior to the treatment that places the subject at risk of developing mucositis.

27. The method of claim 25, wherein administration occurs concurrently with the treatment that places the subject at risk of developing mucositis.

28. The method of claim 25, wherein administration occurs after the treatment that places the subject at risk of developing mucositis.

29. The method of claim 25, wherein the treatment that places the subject at risk of developing mucositis comprises radiation therapy.

30. The method of claim 29, wherein the radiation is selected from the group consisting of x ray radiation and gamma radiation.

31. The method of claim 25, wherein the treatment that places the subject at risk of developing mucositis comprises chemotherapy.

32. The method of claim 25, wherein the composition is administered for one or more days or weeks prior to the treatment.

33. The method of claim 25, wherein the composition is administered for one week prior to treatment and for one or more days after the treatment.

34. The method of claim 25, wherein the composition is administered daily for one week prior to and for four weeks after the treatment.

* * * * *